US011168116B2

(12) United States Patent
Schmidt

(10) Patent No.: US 11,168,116 B2
(45) Date of Patent: Nov. 9, 2021

(54) STREPTAVIDIN MUTEINS AND METHODS OF USING THEM

(71) Applicant: IBA LIFESCIENCES GMBH, Göttingen (DE)

(72) Inventor: Thomas Schmidt, Adelebsen (DE)

(73) Assignee: IBA LIFESCIENCES GMBH, Göttingen (DE)

( * ) Notice: Subject to any disclaimer, the term of this patent is extended or adjusted under 35 U.S.C. 154(b) by 0 days.

(21) Appl. No.: 16/091,079

(22) PCT Filed: Apr. 25, 2017

(86) PCT No.: PCT/EP2017/059715
§ 371 (c)(1),
(2) Date: Oct. 3, 2018

(87) PCT Pub. No.: WO2017/186669
PCT Pub. Date: Nov. 2, 2017

(65) Prior Publication Data
US 2019/0112344 A1    Apr. 18, 2019

(30) Foreign Application Priority Data

Apr. 25, 2016 (EP) ..................................... 16166773

(51) Int. Cl.
| C07K 14/36 | (2006.01) |
| C07K 17/00 | (2006.01) |
| C07K 1/22  | (2006.01) |

(52) U.S. Cl.
CPC ............... *C07K 14/36* (2013.01); *C07K 1/22* (2013.01); *C07K 17/00* (2013.01); *C07K 2319/22* (2013.01)

(58) Field of Classification Search
None
See application file for complete search history.

(56) References Cited

U.S. PATENT DOCUMENTS

| 5,506,121 | A   |   | 4/1996  | Skerra et al. |           |
|-----------|-----|---|---------|---------------|-----------|
| 6,103,493 | A   |   | 8/2000  | Skerra et al. |           |
| 7,981,632 | B2  |   | 7/2011  | Schmidt       |           |
| 10,065,996| B2  | * | 9/2018  | Schmidt       | G01N 33/68|
| 2018/0346527 | A1 | * | 12/2018 | Schmidt     | G01N 33/68|

FOREIGN PATENT DOCUMENTS

| EP | 0835934 A2     | 4/1998  |
| WO | 1997/11183     | 3/1997  |
| WO | 02077018 A1    | 10/2002 |
| WO | 2013/017954    | 2/2013  |
| WO | 2014/076277    | 5/2014  |

OTHER PUBLICATIONS

International Search Report dated Jul. 27, 2017 in PCT/EP2017/059715 (5 pages).
Written Opinion dated Jul. 27, 2017 in PCT/EP2017/059715 (6 pages).
Reznik Go et al: "Streptavidins With Intersubunit Crosslinks Have Enhanced Stability", Nature Biotechnology, Gale Group Inc, US, vol. 14, Aug. 1, 1998, pp. 1007-1011.
Aslan et al: "Engineering a novel, stable dimeric streptavidin with lower isoelectric point", Journal of Biotechnology, Elsevier, Amsterdam, NL, vol . 128, No. 2, Jan. 13, 2007, pp. 213-225.
Voss S et al: "Mutagenesis of a flexible loop in streptavidin leads to higher affinity for the Strep-tag II peptide and improved performance in recombinant protein purification", Protein Engineering, Oxford University Press, Surrey, GB, vol. 10, No. 8, Aug. 1, 1997, pp. 975-982.
Sano T et al: "Intersubunit Contacts Made by Tryptophan-120 With Biotin Are Essential for Both Strong Biotin Binding and Biotin-Induced Tighter Subunit Association of Streptavidin", Proceedings National Academy of Sciences PNAS, National Academy of Sciences, US, vol. 92, Apr. 1, 1995, pp. 3180-3184.
Schmidt and Skerra, "The Strep-tag system for one-step purification and high-affinity detection or capturing of proteins", Nature Protocols, 2007, 2(6):1528-1535.
Young et al., "Recombinant protein expression and purification: A comprehensive review of affinity tags and microbial applications", Biotechnol. J., 2012, 7, 620-634.
Argarana et al., Molecular Cloning and Nucleotide Sequence of the Streptavidin Gene. Nucleic Acids Res. Feb. 25, 1986;14(4):1871-1882.
Bornholst and Falke, Purification of Proteins Using Polyhistidine Affinity Tags. Methods Enzymol. 2000;326:245-254.
Fletcher et al., Self-assembly of proteins and their nucleic acids. J Nanobiotechnology. Jan. 28, 2003;1(1):1 (16 pages).
Knabel et al., Reversible MHC multimer staining for functional isolation of T-cell populations and effective adoptive transfer. Nat Med. Jun. 2002;8(6):631-637.
Schmidt and Skerra, One-step affinity purification of bacterially produced proteins by means of the "Strep tag" and immobilized recombinant core streptavidin. J Chromatogr A. Aug. 5, 1994;676(2):337-345.
Schmidt and Skerra, The Strep-tag System for One-Step Purification and High-Affinity Detection or Capturing of Proteins. Nat Protoc. 2007;2(6):1528-1535.

\* cited by examiner

*Primary Examiner* — Christina Bradley
(74) *Attorney, Agent, or Firm* — Acuity Law Group, P.C.Q; Michael A. Whittaker

(57) ABSTRACT

The invention concerns novel streptavidin muteins and their use for determination, isolation or purification of proteins under denaturing conditions. In one embodiment such a mutein has an Cys residue at sequence position 127 of the wild-type sequence of streptavidin and comprises at least one mutation in the region of the amino acid positions 115 to 121 with reference to the amino acid sequence of wild type streptavidin.

6 Claims, 7 Drawing Sheets
Specification includes a Sequence Listing.

Fig. 1A amino acid sequence of mature wild-type streptavidin (residues 1 to 159; SEQ ID NO: 1)

```
DPSKDSKAQV SAAEAGITGT WYNQLGSTFI VTAGADGALT GTYESAVGNA
        10         20         30         40         50
ESRYVLTGRY DSAPATDGSG TALGWTVAWK NNYRNAHSAT TWSGQYVGGA
        60         70         80         90        100
EARINTQWLL TSGTTEANAW KSTLVGHDTF TKVKPSAASI DAAKKAGVNN
       110        120        130        140        150
GNPLDAVQQ
      159
```

Fig. 1B amino acid sequence of N- and C-terminally shortened wild-type streptavidin (residues 14 to 139; SEQ ID NO: 2, also known as core streptavidin)

```
14
EAGITGTWYNQLGSTFIVTAGADGALTGTYESAVGNAESRYVLTGRYDSAPATDGSGTALGW
TVAWKNNYRNAHSATTWSGQYVGGAEARINTQWLLTSGTTEANAWKSTLVGHDTFTKVKPSA
AS
 139
```

Fig. 2

```
            Position:    117 118 119 120 121

Motif1 (SEQ ID NO: 98):  Glu Asn Ala Gly Phe
                         Asp             Tyr
                         Arg             Met
                         His
                         Asn
                         Gln
                         Thr
                         Ser
                         Leu
                         Met 117 118 119 120 121

Motif2 (SEQ ID NO: 99):  Tyr Asn Ala Tyr Leu
                         Phe         Phe Ile
                         Arg         Leu Met
                         Trp         Ile Gln
                         Gln         Met Gly
                         Trp
                         Ser
                         Ala
                         Val Motif3 (SEQ ID NO: 101): His --- --- Trp Tyr
                         Glu         Val Leu
                         Gln             Met
                         Thr             Arg
                         Ala             Thr
                         Ile             Ser
                         Arg             Phe
                         Asn
                         Lys
                         Ser
```

Fig. 3

```
              14        20        30        40        50        60        70        80        90       100       110       120       130      139
               |         |         |         |         |         |         |         |         |         |         |         |         |        |
Wt:           EAGITGTWYNQLGSTFIVTAGADGALTGTYESAVGNAESRYVLTGRYDSAPATDGSGTALGWTVAWKNYRNAHSATTWSGQYVGGAEARINTQWLLTSGTTEANAWKSTLVGHDTFTKVKPSAAS
Mutein"1":    EAGITGTWYNQLGSTFIVTAGADGALTGTYVTARGNAESRYVLTGRYDSAPATDGSGTALGWTVAWKNYRNAHSATTWSGQYVGGAEARINTQWLLTSGTTEANAWKSTLVGHDTFTKVKPSAAS
Mutein m302:  EAGITGTWYNQLGSTFIVTAGADGALTGTYVTARGNAESRYVLTGRYDSAPATDGSGTALGWTVAWKNYRNAHSATTWSGQYVGGAEARINTQWLLTSGTTEH--WYSTLVGHDTFTKVKPSAAS
Mutein m302C: EAGITGTWYNQLGSTFIVTAGADGALTGTYVTARGNAESRYVLTGRYDSAPATDGSGTALGWTVAWKNYRNAHSATTWSGQYVGGAEARINTQWLLTSGTTEH--WYSTLVGCDFTKVKPSAAS
Mutein m1-9:  EAGITGTWYNQLGSTFIVTAGADGALTGTYVTARGNAESRYVLTGRYDSAPATDGSGTALGWTVAWKNYRNAHSATTWSGQYVGGAEARINTQWLLTSGTTEENAGYSTLVGHDTFTKVKPSAAS
Mutein m1-9C: EAGITGTWYNQLGSTFIVTAGADGALTGTYVTARGNAESRYVLTGRYDSAPATDGSGTALGWTVAWKNYRNAHSATTWSGQYVGGAEARINTQWLLTSGTTEENAGYSTLVGCDFTKVKPSAAS
```

Mutein "1": SEQ ID NO: 12
Mutein m302: SEQ ID NO: 13
Mutein m302C: SEQ ID NO: 14
Mutein m1-9: SEQ ID NO: 15
Mutein m1-9C: SEQ ID NO: 16

Fig. 6
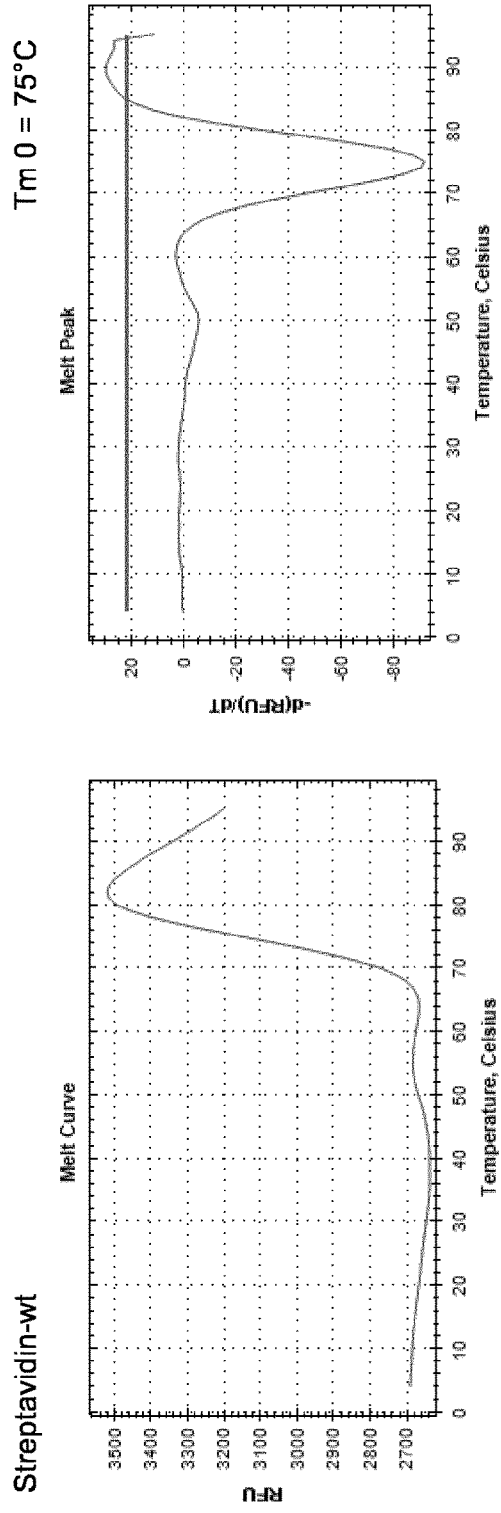
Streptavidin-wt
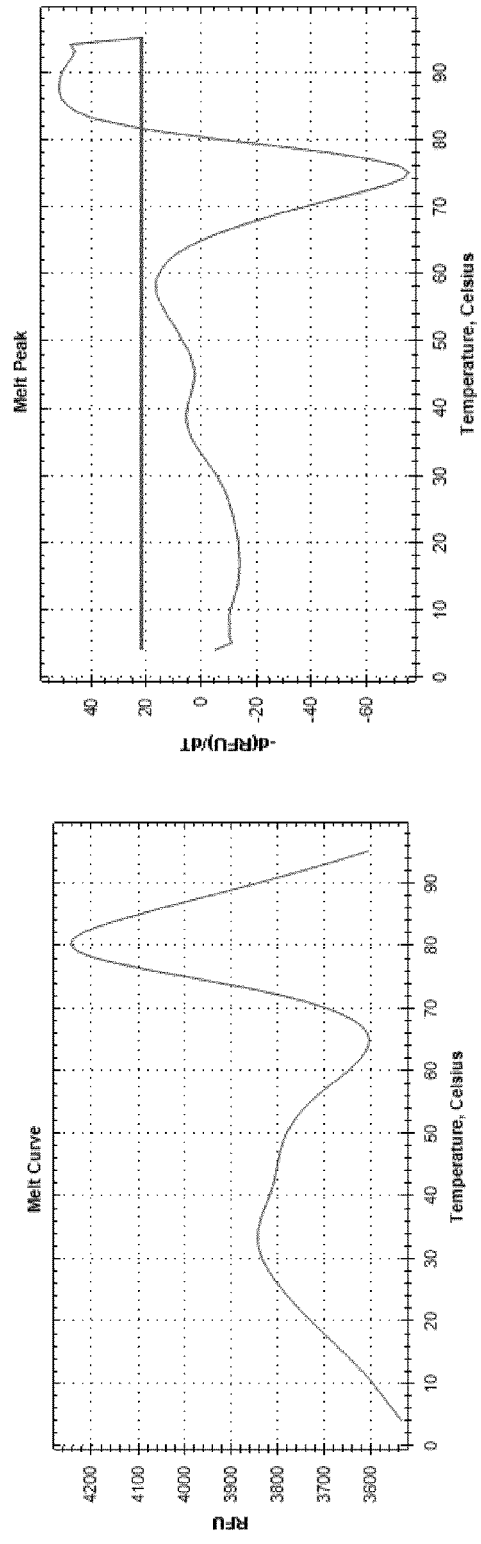
Mutein 1

Fig. 6 (continued)
Mutein m1-9
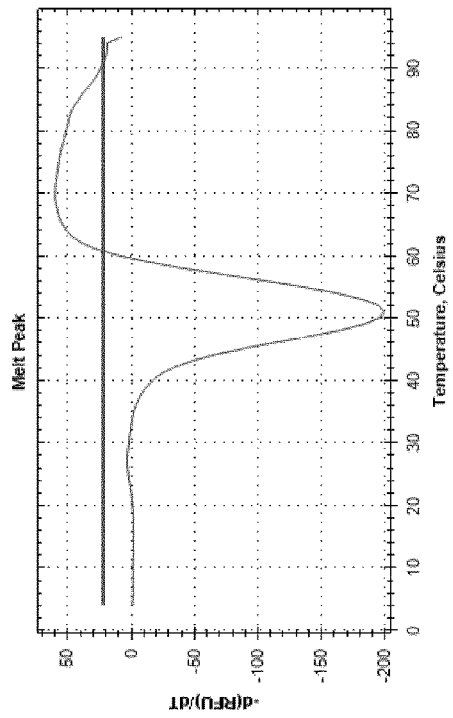
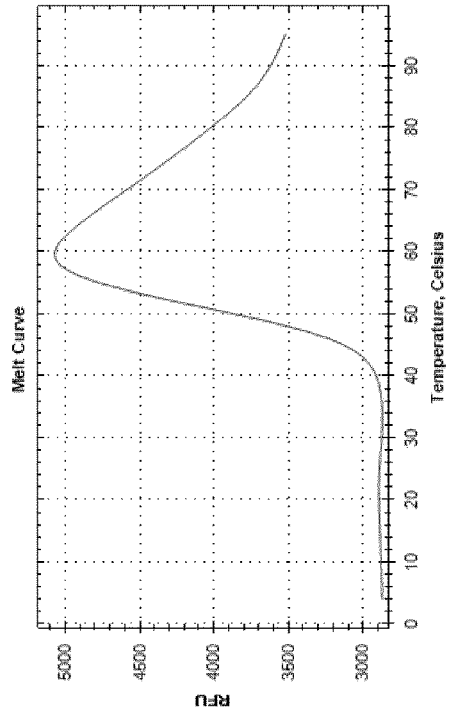
Mutein m1-9C
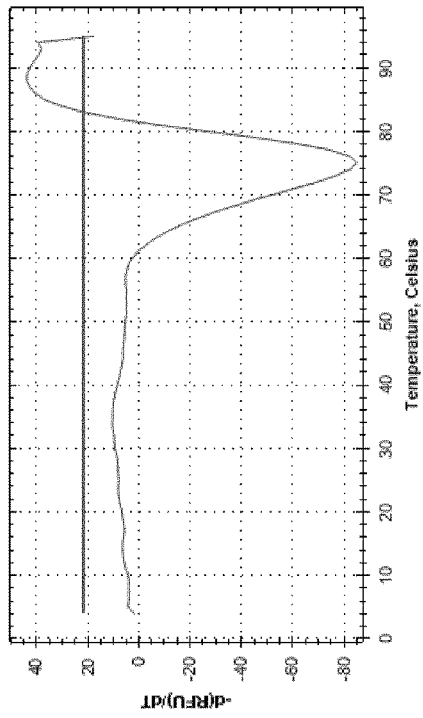
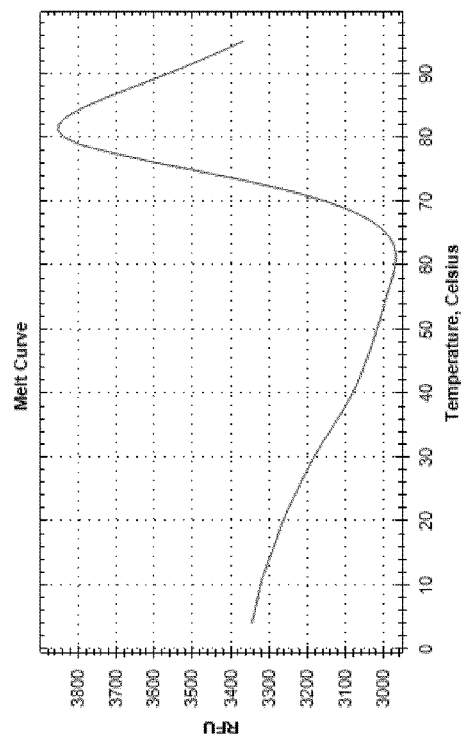

STREPTAVIDIN MUTEINS AND METHODS OF USING THEM

CROSS-REFERENCE TO RELATED APPLICATIONS

The present invention is filed under 35 U.S.C. § 371 as the U.S. national phase of International Application No. PCT/EP2017/059715, filed Apr. 25, 2017, which designated the U.S. and claims the right of priority of European patent application 16 166 773.8 filed with the European Patent Office on Apr. 25, 2016 purposes. The entire disclosures of the above-identified priority applications are hereby fully incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 3, 2018, is named SCH-4600-US_SeqListing.txt and is 27 kilobytes in size.

FIELD OF THE INVENTION

The present invention relates to novel stabilized streptavidin muteins, methods of producing such muteins by means of recombinant DNA technology as well as the use of these streptavidin muteins for the isolation, purification and determination of biological substances such as recombinant proteins under denaturing conditions. The invention thus also relates to solid phases having immobilized thereon the streptavidin muteins of the invention as well as to nucleic acid molecules encoding the muteins of the invention. The invention further relates to kits, suitable for detection, isolation or purification of proteins, containing muteins of the invention, for example, immobilized on a solid phase.

BACKGROUND

High-level expression of many recombinant proteins in *Escherichia coli* leads to the formation of highly aggregated protein commonly referred to as inclusion bodies. Inclusion bodies are normally formed in the cytoplasm. However, when a secretion vector is used, they can also form in the periplasmic space. Inclusion bodies are however, not restricted to *E. coli*; they can also form in yeast, mammalian, and insect cells, for example. In case of the formation of inclusion bodies, fusion proteins carrying polyhistidine affinity tags can be purified by the use of denaturing conditions such as 6 M guanidinium hydrochloride (also known as guanidine hydrochloride) or 8 M urea during the purification process (see, for example, Palmer & Wingfield "Preparation and Extraction of Insoluble Inclusion-Body Proteins from *Escherichia coli*", Curr Protoc Protein Sci. 2004 November; CHAPTER: Unit-6.3. doi:10.1002/0471140864.ps0603s38 or Bornholst & Falke "Purification of Proteins Using Polyhistidine Affinity Tags", Methods Enzymol. 2000; 326: 245-254). Interaction of the affinity chromatography resin with the polyhistidine tag such as a hexahistidine ($His_6$) tag does not require a specific conformation of the peptide tag, which makes effective purification with the use of denaturing conditions possible. For this reason, the $His_6$ tag has been seen by Schmidt and Skerra as the better alternative for isolation of recombinant proteins from solubilized inclusion bodies in the presence of, for example, 6 M guanidine hydrochloride than the STREP-TAG® II (IBA GmbH) affinity tag (Schmidt & Skerra, "The strep-tag system for one-step purification and high-affinity detection or capturing of proteins." Nature Protocols 2 (2007), 1528-1535). When using a streptavidin binding affinity tag such as the STREP-TAG® affinity tag, it has thus been recommended to fuse both such a streptavidin binding affinity tag and a $His_6$ tag to a recombinant protein, to be able to purify the recombinant protein from inclusion bodies first under denaturing conditions by means of the $His_6$ tag and, after refolding of the protein, follow up with a second affinity purification under physiological conditions by means of the streptaividin binding peptide. So doing should provide the ability of obtaining highly pure and homogenous protein preparations from inclusion bodies.

Apart from the limitation of not being suitable for protein purification under denaturing conditions, the STREP-TAG®II affinity tag (Schmidt & Skerra, Nature Protocols 2 (2007), supra or U.S. Pat. No. 5,506,121) that has the sequence Trp-Ser-His-Pro-Gln-Phe-Glu-Lys, SEQ ID NO: 3) has been widely recognized as a very versatile affinity tag. The STREP-TAG®II affinity tag is particularly popular for providing recombinant proteins at high purity and functionality by using physiological conditions within a rapid one-step protocol. The currently most widely and most efficient streptavidin based receptor for the STREP-TAG®II affinity tag are streptavidin muteins with improved binding affinity that are named STREP-TACTIN® (IBA GmbH) (Voss & Skerra, Protein Engineering 10 (1997), 975-982; U.S. Pat. No. 6,103,493 or European Patent 0 835 934). The STREP-TAG®II affinity tag binds to the biotin binding pocket of streptavidin (and these streptavidin muteins) enabling mild competitive elution with biotin derivatives, preferably desthiobiotin, for repeated use of the affinity resins. The system consisting of the STREP-TAG®II affinity tag and the STREP-TACTIN® streptavidin mutein has provided powerful applications in the last over 15 years for purification, detection and assay of recombinant proteins (reviewed in Schmidt & Skerra, Nature Protocols 2, supra) and even of cells (Knabel et al., "Reversible MHC multimer staining for functional isolation of T-cell populations and effective adoptive transfer", Nature Medicine 8 (2002), 631-637).

For this reason, it would be desirable to have at hand a tool and a system that allows purification of fusion proteins under denaturing conditions by means of affinity chromatography using streptavidin binding affinity peptides. It is therefore an object of the present invention to provide a tool and a system that allows purification of fusion proteins under denaturing conditions by means of streptavidin based affinity chromatography.

SUMMARY OF THE INVENTION

In a first aspect the invention provides a mutein, selected from muteins of streptavidin, wherein the mutein
(a) has a Cys residue at sequence position 127 with reference to the amino acid sequence of wild-type streptavidin as set forth in SEQ ID NO: 1 and
(b) comprises at least one mutation in the region of the amino acid positions 115 to 121 with reference to the amino acid sequence of wild type streptavidin as set forth in SEQ ID NO: 1.

In a second aspect, the invention provides a nucleic acid molecule, comprising a sequence coding for a streptavidin mutein of the invention, i.e. a streptavidin mutein that
(a) has a Cys residue at sequence position 127 with reference to the amino acid sequence of wild-type streptavidin as set forth in SEQ ID NO: 1 and (b) comprises at least one mutation in the region of the amino acid positions 115 to 121 with reference to the amino acid sequence of wild type streptavidin as set forth in SEQ ID NO: 1.

The nucleic acid of this second aspect of the invention might be a vector comprising at least one copy of such nucleic acid molecule in an operatively functionally environment.

In a third aspect, the invention provides a cell that is transformed or transfected with a nucleic acid or a vector according to the second aspect.

The invention also provides a method of producing a streptavidin mutein according to the first aspect, comprising:
(a) transforming a suitable host cell with a vector which contains a nucleic acid coding for the streptavidin mutein,
(b) culturing the host cell under conditions in which an expression of the streptavidin mutein takes place,
(c) isolating the mutein.

The invention also provides a method of isolating, purifying or determining under denaturing conditions a protein that is fused with a) a peptide sequence of the formula Trp-Xaa-His-Pro-Gln-Phe-Yaa-Zaa (SEQ ID NO: 8) in which Xaa represents an arbitrary amino acid and Yaa and Zaa either both denote Gly or Yaa denotes Glu and Zaa denotes Arg or Lys or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa- (SEQ ID NO: 9) where Oaa is Trp, Lys or Arg, Xaa is any amino acid and where either Yaa and Zaa are both Gly or Yaa is Glu and Zaa is Lys or Arg, comprising contacting a sample containing said protein with a streptavidin mutein as described herein, under suitable conditions to bind the peptide sequence to the streptavidin mutein, and separating the resulting complex from said sample.

The invention also provides a method of immobilizing under denaturing conditions a protein which is fused with a) a peptide sequence of formula Trp-Xaa-His-Pro-Gln-Phe-Yaa-Zaa (SEQ ID NO: 8) in which Xaa represents an arbitrary amino acid and Yaa and Zaa either both denote Gly or Yaa denotes Glu and Zaa denotes Arg or Lys or b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa-(SEQ ID NO: 9) where Oaa is Trp, Lys or Arg, Xaa is any amino acid and where either Yaa and Zaa are both Gly or Yaa is Glu and Zaa is Lys or Arg, comprising contacting said protein to a solid phase which carries a streptavidin mutein according to the first aspect, under conditions for immobilizing said protein.

The invention also provides a solid phase having immobilized thereon comprising a streptavidin mutein of the invention. Such a solid phase may be an affinity chromatography matrix.

The invention further provides a reagent kit comprising a streptavidin mutein as described herein or a solid phase having immobilized thereon a streptavidin as described herein. Such a kit may further comprise at least one reagent selected from the group consisting of a conventional buffer, an auxiliary substance and an additive. The invention also provides a streptavidin mutein as described herein immobilized on a solid support such as a chromatography resin, an ELISA plate or a chip for surface plasmon resonance (SPR) measurements.

These aspects of the invention will be more fully understood in view of the following description, drawings and non-limiting examples.

DETAILED DESCRIPTION

It has been found in the present invention that the replacement of the histidine residue that is present at sequence position 127 of wild-type streptavidin provide muteins that allow the purification of fusion proteins by means of streptavidin binding peptides under denaturing conditions. This finding is in particular surprising since the replacement of His 127 by a cystein residue in wild-type streptavidin has lead to an only insignificant increase in stability of streptavidin in 7 M guanidine hydrochloride (Reznik et al., "Streptavidins with intersubunit crosslinks have enhanced stability", Nat Biotechnol. 1996 August; 14(8):1007-11.). It could have thus not been expected that this amino acid exchange will enable streptavidin muteins that reversibly bind streptavidin binding peptides to be used for protein purification by affinity chromatography under denaturing conditions. This holds in particular true, since in accordance with the recommendation of Schmidt & Skerra, Nature Protocols 2, supra to use $His_6$ tags/immobilized metal chelate affinity chromatography (IMAC) for protein purification under denaturing conditions, it has also been found in the present invention that the streptavidin mutein "1" of U.S. Pat. No. 6,103,493 (that has the amino sequence $Val^{44}$-$Thr^{45}$-$Ala^{46}$-$Arg^{47}$ (SEQ ID NO: 10) at amino acid positions 44 to 47 of the wt-streptavidin sequence, while being significantly more stable under physiological conditions than muteins of the present invention, is not suitable for protein purification under denaturing conditions (cf. Examples 4 and 5 of the present application). It has rather been found here that streptavidin muteins which comprise at least one mutation in the region of the amino acid positions 115 to 121 with reference to the amino acid sequence of wild type streptavidin as set forth in SEQ ID NO: 1 profit from the replacement of His 127 by Cys. Such streptavidin muteins comprising at least one mutation in the region of the segment of amino acid positions 115 to 121 have been described in International patent application WO 20140/76277. Accordingly, the present invention has the advantage that it abolishes the need to fuse both a streptavidin binding affinity tag and a His6 tag to a recombinant protein in case the protein will form inclusion bodies during its production.

As an added advantage, the muteins of the present invention are stable under denaturing conditions such as exposure to 4 M guanidinium hydrochloride as well as to exposure to strong bases such as NaOH (see Example 4). Accordingly, the muteins of the present invention can also be advantageously used in applications such as biosensors for e.g. ForteBio's OCTET® or GE's BIACORE® family of instruments that provide label-free, real-time measurements for the analysis of protein:protein, protein:peptide, and protein:small molecule interactions or chips for high throughput analysis of a multitude of analytes bound to its surface or beads such as magnetic beads or ALPHASCREEN® (PerkinElmer Life Sciences, Inc.) beads or LUMINEX® (Luminex Corporation) beads for e.g. protein:protein interaction analysis. In all such examples, the coating of the respective solid phase with a streptavidin mutein described provides a generic platform for the simple, reproducible, mild and stable immobilization of an arbitrary protein to said solid phase. At the same time, the stability of the streptavidin muteins to high concentrations of alkali (hydroxide ions) allow regeneration of the solid phase for further use.

The streptavidin muteins of the present invention may correspond to the amino acid sequence of wt-streptavidin outside the region of the amino acid positions 115-121 and apart from the presence of the cysteine residue at sequence position 127. On the other hand, the amino acid sequence according to the invention can also be different to the wt-streptavidin sequence outside the region of the amino acids 115 to 121. Such variants of the streptavidin sequence include naturally occurring as well as artificially produced variants and the modifications are understood as substitution including those disclosed by U.S. Pat. No. 6,103,493, those containing a disulfide bond, insertions, deletions of amino acid residues as well as N- or/and C-terminal deletions or additions.

Preferred streptavidin muteins according to the invention comprise at least one mutation at the amino acid positions 117, 120 and 121 and/or comprise a deletion of amino acids 118 and 119 and substitution of at least of amino acid position 121.

It is noted in this context that deletion of amino acids in loops may not only be tolerated but may even be favorable for purification of fusion proteins carrying streptavidin binding peptides. Accordingly, streptavidin muteins containing additional deletions, substitutions or additions outside the preferred changes at the positions specified within the present invention also fall within the scope of the present invention.

Thus, the term "mutation" as used herein also includes a deletion of an amino acid residue (however, the Cys residue at position 127 of the wild-type sequence of streptavidin will always be present in a mutein of the invention). In this respect, it is however noted that a streptavidin mutein in which the entire loop of the amino acids 114 to 121 of streptavidin (TTEANAWK) or the loop region of amino acids 115 to 121 of streptavidin (TEANAWK) is deleted is not encompassed in the present invention. Rather in the muteins of the invention that contain one or more mutations within the segment of amino acids 115 to 121, at least one amino acid is present at one of the position 115 to 121. In some of these embodiments, an amino acid is present at positions 117, 118, 119, 120 and 121 while the amino acid at position 118 and/or 119 is deleted. Thus, in such muteins the segment formed by sequence positions 115 to 121 is shorted by either one or two amino acids. In line with the above disclosure that muteins in which the entire segment of amino acids 115 to 121 is deleted are not being used in the present invention, the muteins of streptavidin as described in Fletcher et al, Journal of Biotechnology 2003, are not encompassed by the present invention. This means that the following streptavidin muteins are excluded herein: 1. A mutein in which the wild type amino acid residues Thr-Thr-Glu-Asp-Asn-Ala-Trp-Lys (TTEANAWK, SEQ ID NO: 17) at sequence positions 114 to 121 are deleted. This mutein is designated SAPV in Fletcher et al. 2. The two muteins designated SAPV-Alb5 and SAPV-84 in Fletcher et al in which the deleted nine amino acid residues Thr-Thr-Glu-Asp-Asn-Ala-Trp-Lys (SEQ ID NO: 17) are replaced by the amino acid sequence HPYFYAPELLFFAK (SEQ ID NO: 18) or EGGKETLTPSELRDLV (SEQ ID NO: 19).

Preferred streptavidin muteins of the invention are derived from streptavidin variants which are shortened at the N- or/and the C-terminus. The minimal streptavidins which are N- and C-terminally shortened known from the state of the art are particularly preferred. A preferred polypeptide according to the present invention comprises outside of the mutagenized region the amino acid sequence of a minimal streptavidin which begins N-terminally in the region of the amino acid positions 10 to 16 and terminates C-terminally in the region of the amino acid positions 133 to 142. Such a streptavidin mutein polypeptide corresponds preferably to a minimal streptavidin outside of the mutation region which comprises an amino acid sequence from position Ala13 to Ser139 and optionally has an N-terminal methionine residue instead of Ala13. In this application the numbering of amino acid positions refers throughout to the numbering of mature wt-streptavidin (Argarana et al., Nucleic Acids Res. 14 (1986), 1871-1882, cf. also FIG. 1 and SEQ ID NO: 1 and NO: 2) which is also deposited under accession number UniProtKB—P22629.

Streptavidin muteins carrying one or more mutations in the region of the amino acid positions 115 to 121 according to the invention that are especially preferred may be characterized in different subclasses.

First, amino acids that are found at positions 117, 120, and 121 can be regarded separately depending on the presence or non-presence of the deletion of the two amino acids at positions 118 and 119. Amino acids that are found at positions 117, 120, and 121 in these two different cases and which, therefore, may contribute to binding of streptavidin binding peptides in each case, are summarized in FIG. 2.

Muteins without deletion may be characterized as follows: They carry at position 117 most preferably a large hydrophobic residue like Trp, Tyr or Phe or a charged residue like Glu, Asp or Arg or a hydrophilic residue like Asn or Gln, or, less preferred, the hydrophobic residues Leu, Met or Ala, or the polar residues Thr, Ser or His, in combination with i) a small residue like Ser or Ala or, most preferably, Gly at position 120 which is then combined with a hydrophobic residue at position 121, most preferably with a bulky hydrophobic residue like Trp, Tyr or Phe or in combination with ii) a hydrophobic residue at position 120 which is Leu, Ile, Met, or Val or, more preferably, Tyr or Phe, which is then combined with a small residue like Gly, Ala, or Ser, or with Gin, or with a hydrophobic residue like Leu, Val, Ile, Trp, Tyr, Phe, or Met at position 121.

Muteins with deleted amino acid positions 118 and 119 may be characterized as follows: Position 117 may be any amino acid with bulky hydrophobic residues like Phe, Tyr or Trp being less preferred and position 120 is then most preferably a Trp and less preferably Val and position 121 is also a hydrophobic amino acid, most preferably Met, Leu, Tyr or Phe, or position 121 is a small hydrophilic residue, most preferably Ser or Thr, or position 121 is Arg. An overview of illustrative specific mutein sequences is also shown in Tables 1-5 given below.

In some embodiments, a streptavidin mutein of the invention has a first sequence motif for positions 117, 120, and 121 at the sequence 117 to 121 of the wild type sequence that comprises a Gly residue at sequence position 120 ($Gly^{120}$) as most important feature. Such a motif carries preferably a Phe or a Tyr, or less preferably a Met residue at sequence position 121 and a Glu, an Asp, an Arg, a His, a Leu, a Met, an Asn, a Gln, a Thr or a Ser residue at sequence position 117, position 117 thus being more variable in this motif. Such a mutein may have the wild type streptavidin amino acid $Asn^{118}$ and/or $Ala^{119}$ at sequence positions 118 and 119 (see also FIG. 2). It is however also within the scope of the present invention that $Asn^{118}$ and $Ala^{119}$ are replaced by another amino acid residue. This mutation might be either a conservative substitution (replacing Asn$^{118}$ by Gln or Asp, for example, or Ala$^{119}$ by Ser, Val or Ile, for example) or a non-conservative substitution (replacing Asn$^{118}$ by a positively charged or hydrophobic amino acid residue, for example). This motif1 may be thus characterized by the following consensus sequence1: Xaa$^{117}$Gly$^{120}$Yaa$^{121}$, wherein Xaa may be any amino acid and Yaa may be Phe or Tyr or Met.

In a second sequence motif for positions 117 to 121 a streptavidin mutein disclosed here comprises a hydrophobic or aromatic amino acid residue at sequence position 120 (see also FIG. 2). This hydrophobic or aromatic amino acid at sequence position 120 is preferably a Tyr, a Phe, a Leu, an Ile or a Met. In this second sequence motif, a hydrophobic or aromatic amino acid may also be present (independently selected from position 120) at sequence position 121. Preferred residues at position 121 are Leu, Ile, and Met, less preferred are a Gly, a Gln, a Trp, a Ser, an Ala or a Val. In addition, such a mutein may also have, independent from the sequence positions 120 and 121, a mutation at sequence position 117. Preferred mutations at sequence position 117 are a Tyr or a Phe, less preferred are an Arg, a Trp or a Gln residue. Also such a mutein of this second sequence motif may either have the wild type streptavidin amino acid Asn$^{118}$ and/or Ala$^{119}$ or a mutated residue at sequence positions 118 and 119. This motif2 may be thus characterized by the following consensus sequence2: Aaa$^{117}$Baa$^{120}$Caa$^{121}$, wherein Aaa may be Tyr, Phe, Arg, Trp or Gln, Baa may be Tyr, Phe, Leu, Ile or Met and Caa may be any amino acid.

In a third sequence motif for streptavidin muteins disclosed here having mutations at sequence positions 117 to 121 the residues at sequence positions 118 and 119 are deleted (see also FIG. 2). In this context, at sequence position 117 a His, a Glu, a Gln, a Thr, an Arg, an Asn, a Lys, a Ser, an Ala or an Ile residue are preferred, at sequence position 120, the highly preferred amino acid is then a Trp or, less preferred, a Val residue and at sequence position 121 a Tyr, a Leu, a Met, a Thr, a Ser, a Phe or an Arg residue are preferred. This motif3 may be thus characterized by the following consensus sequence3: Daa$^{117}$Eaa$^{118}$Faa$^{119}$Gaa$^{120}$Haa$^{121}$, wherein Daa and Haa may be any amino acid and Eaa and Faa are both deleted and Gaa may be Trp or Val.

However, by no means should the consensus sequences 1 to 3 explained above and shown in FIG. 2 be regarded as limiting for mutations of suitable muteins of the invention in the region of sequence positions 117 to 121 of wt-streptavidin. Further illustrative examples of mutations within this segment are shown in the following Tables 1 to 5. It is noted here that streptavidin muteins having such mutations and their ability to bind streptavidin binding peptides have been described for the first time in the International Patent Application WO 2014/076277.

Tables 1 to 5: Examples of mutations of muteins of the invention at sequence positions 117 to 121 of the amino acid sequence of wt-streptavidin

TABLE 1

| | |
|---|---|
| Wt streptavidin (SEQ ID NO: 20) | Ala$^{117}$Asn$^{118}$Ala$^{119}$Trp$^{120}$Lys$^{121}$ |
| mutein "1" | Ala$^{117}$Asn$^{118}$Ala$^{119}$Trp$^{120}$Lys$^{121}$ |
| m36 (SEQ ID NO: 21) | Tyr$^{117}$Asn$^{118}$Ala$^{119}$Phe$^{120}$Met$^{121}$ |

TABLE 1-continued

| | |
|---|---|
| m23 (SEQ ID NO: 22) | Tyr$^{117}$Asn$^{118}$Ala$^{119}$Tyr$^{120}$Ala$^{121}$ |
| m41 (SEQ ID NO: 23) | Ala$^{117}$---$^{118}$---$^{119}$Trp$^{120}$Tyr$^{121}$ |
| m4 (SEQ ID NO: 24) | Asp$^{117}$Asn$^{118}$Ala$^{119}$Gly$^{120}$Phe$^{121}$ |
| m12 (SEQ ID NO: 25) | Arg$^{117}$Asn$^{118}$Ala$^{119}$Gly$^{120}$Phe$^{121}$ |
| m22 (SEQ ID NO: 26) | Gln$^{117}$Asn$^{118}$Ala$^{119}$Gly$^{120}$Phe$^{121}$ |
| m31 (SEQ ID NO: 27) | Phe$^{117}$Asn$^{118}$Ala$^{119}$Ser$^{120}$Trp$^{121}$ |
| m32 (SEQ ID NO: 28) | Asp$^{117}$Asn$^{118}$Ala$^{119}$Val$^{120}$Met$^{121}$ |
| m35 (SEQ ID NO: 29) | Ala$^{117}$---$^{118}$---$^{119}$Trp$^{120}$Met$^{121}$ |
| m38 (SEQ ID NO: 30) | Glu$^{117}$Asn$^{118}$Ala$^{119}$Gly$^{120}$Phe$^{121}$ |
| m40 (SEQ ID NO: 31) | Tyr$^{117}$Asn$^{118}$Ala$^{119}$Tyr$^{120}$Ser$^{121}$ |
| m42 (SEQ ID NO: 32) | Phe$^{117}$Asn$^{118}$Ala$^{119}$Tyr$^{120}$Gly$^{121}$ |
| m45 (SEQ ID NO: 33) | Tyr$^{117}$Asn$^{118}$Ala$^{119}$Gly$^{120}$Phe$^{121}$ |
| m46 (SEQ ID NO: 34) | Arg$^{117}$Asn$^{118}$Ala$^{119}$Tyr$^{120}$Ala$^{121}$ |
| m47 (SEQ ID NO: 35) | Trp$^{117}$Asn$^{118}$Ala$^{119}$Tyr$^{120}$Gly$^{121}$ |
| m7 (SEQ ID NO: 36) | Leu$^{117}$Asn$^{118}$Ala$^{119}$Gly$^{120}$Phe$^{121}$ |
| m10 (SEQ ID NO: 37) | His$^{117}$Asn$^{118}$Ala$^{119}$Gly$^{120}$Tyr$^{121}$ |
| m17 (SEQ ID NO: 38) | Met$^{117}$Asn$^{118}$Ala$^{119}$Gly$^{120}$Phe$^{121}$ |
| m21 (SEQ ID NO: 39) | Arg$^{117}$Asn$^{118}$Ala$^{119}$Gly$^{120}$Tyr$^{121}$ |
| m24 (SEQ ID NO: 40) | Glu$^{117}$Asn$^{118}$Ala$^{119}$Gly$^{120}$Trp$^{121}$ |
| m27 (SEQ ID NO: 41) | His$^{117}$Asn$^{118}$Ala$^{119}$Gly$^{120}$Phe$^{121}$ |
| m28 (SEQ ID NO: 42) | Ser$^{117}$Asn$^{118}$Ala$^{119}$Gly$^{120}$Phe$^{121}$ |
| m30 (SEQ ID NO: 43) | Thr$^{117}$Asn$^{118}$Ala$^{119}$Gly$^{120}$Phe$^{121}$ |
| m33 (SEQ ID NO: 44) | Asn$^{117}$Asn$^{118}$Ala$^{119}$Gly$^{120}$Phe$^{121}$ |
| m1 (SEQ ID NO: 45) | Glu$^{117}$Asn$^{118}$Ala$^{119}$Gly$^{120}$Met$^{121}$ |
| m3 (SEQ ID NO: 46) | Trp$^{117}$Asn$^{118}$Ala$^{119}$Cys$^{120}$Cys$^{121}$ |
| m8 (SEQ ID NO: 47) | Met$^{117}$Asn$^{118}$Ala$^{119}$Phe$^{120}$Val$^{121}$ |
| m15 (SEQ ID NO: 48) | Ala$^{117}$Asn$^{118}$Ala$^{119}$Asp$^{120}$Trp$^{121}$ |
| m6 (SEQ ID NO: 49) | Ser$^{117}$Asn$^{118}$Ala$^{119}$Met$^{120}$Met$^{121}$ |
| m9 (SEQ ID NO: 50) | Arg$^{117}$Asn$^{118}$Ala$^{119}$Val$^{120}$Val$^{121}$ |
| m20 (SEQ ID NO: 51) | Ser$^{117}$Asn$^{118}$Ala$^{119}$Ser$^{120}$Phe$^{121}$ |
| m34 (SEQ ID NO: 52) | Ala$^{117}$---$^{118}$---$^{119}$Trp$^{120}$Asp$^{121}$ |
| m14 (SEQ ID NO: 53) | Arg$^{117}$Asn$^{118}$Ala$^{119}$Arg$^{120}$Ala$^{121}$ |
| m18 (SEQ ID NO: 54) | Ser$^{117}$Asn$^{118}$Ala$^{119}$Ala$^{120}$Phe$^{121}$ |
| m19 (SEQ ID NO: 55) | Gly$^{117}$Asn$^{118}$Ala$^{119}$Met$^{120}$Met$^{121}$ |

TABLE 2

| | |
|---|---|
| Wt | Ala$^{117}$Asn$^{118}$Ala$^{119}$Trp$^{120}$Lys$^{121}$ |
| m4001 | Ala$^{117}$Asn$^{118}$Ala$^{119}$Trp$^{120}$Lys$^{121}$ |
| m8 (SEQ ID NO: 56) | Glu$^{117}$Asn$^{118}$Ala$^{119}$Gly$^{120}$Phe$^{121}$ |
| m21 (SEQ ID NO: 57) | Asp$^{117}$Asn$^{118}$Ala$^{119}$Gly$^{120}$Tyr$^{121}$ |

TABLE 2-continued

| | |
|---|---|
| m9 (SEQ ID NO: 58) | Glu$^{117}$Asn$^{118}$Ala$^{119}$Gly$^{120}$Tyr$^{121}$ |
| m1 (SEQ ID NO: 59) | Arg$^{117}$Asn$^{118}$Ala$^{119}$Met$^{120}$Met$^{121}$ |
| m2 (SEQ ID NO: 60) | Arg$^{117}$Asn$^{118}$Ala$^{119}$Gly$^{120}$Phe$^{121}$ |
| m3 (SEQ ID NO: 61) | Ala$^{117}$Asn$^{118}$Ala$^{119}$Pro$^{120}$Ala$^{121}$ |
| m5 (SEQ ID NO: 62) | Ala$^{117}$Asn$^{118}$Ala$^{119}$Met$^{120}$Val$^{121}$ |
| m13 (SEQ ID NO: 63) | Gln$^{117}$Asn$^{118}$Ala$^{119}$Ser$^{120}$Ala$^{121}$ |
| m14 (SEQ ID NO: 64) | Ala$^{117}$Asn$^{118}$Ala$^{119}$Gly$^{120}$Phe$^{121}$ |
| m24 (SEQ ID NO: 65) | Gln$^{117}$Asn$^{118}$Ala$^{119}$Met$^{120}$Val$^{121}$ |
| m4 (SEQ ID NO: 66) | Asn$^{117}$Asn$^{118}$Ala$^{119}$Gly$^{120}$Tyr$^{121}$ |
| m6 (SEQ ID NO: 67) | Ala$^{117}$Asn$^{118}$Ala$^{119}$Ala$^{120}$Val$^{121}$ |
| m7 (SEQ ID NO: 68) | Ser$^{117}$Asn$^{118}$Ala$^{119}$Met$^{120}$Ile$^{121}$ |
| m10 (SEQ ID NO: 69) | His$^{117}$Asn$^{118}$Ala$^{119}$Gly$^{120}$Tyr$^{121}$ |
| m15 (SEQ ID NO: 70) | Ser$^{117}$Asn$^{118}$Ala$^{119}$Met$^{120}$Ala$^{121}$ |
| m23 (SEQ ID NO: 71) | Gln$^{117}$Asn$^{118}$Ala$^{119}$Val$^{120}$Ala$^{121}$ |
| m17 (SEQ ID NO: 72) | Tyr$^{117}$Asn$^{118}$Ala$^{119}$Tyr$^{120}$Met$^{121}$ |
| m12 (SEQ ID NO: 73) | Leu$^{117}$Asn$^{118}$Ala$^{119}$Trp$^{120}$Gly$^{121}$ |
| m20 (SEQ ID NO: 74) | His$^{117}$Asn$^{118}$Ala$^{119}$Ser$^{120}$Met$^{121}$ |

TABLE 3

| | |
|---|---|
| Wt | Ala$^{117}$Asn$^{118}$Ala$^{119}$Trp$^{120}$Lys$^{121}$ |
| mutein "1" | Ala$^{117}$Asn$^{118}$Ala$^{119}$Trp$^{120}$Lys$^{121}$ |
| m101 (SEQ ID NO: 75) | Tyr$^{117}$Asn$^{118}$Ala$^{119}$Phe$^{120}$Leu$^{121}$ |
| m106 (SEQ ID NO: 76) | Phe$^{117}$Asn$^{118}$Ala$^{119}$Phe$^{120}$Leu$^{121}$ |
| m111 (SEQ ID NO: 77) | Tyr$^{117}$Asn$^{118}$Ala$^{119}$Leu$^{120}$Trp$^{121}$ |
| m100 (SEQ ID NO: 78) | Phe$^{117}$Asn$^{118}$Ala$^{119}$Tyr$^{120}$Ile$^{121}$ |
| m110 (SEQ ID NO: 79) | Tyr$^{117}$Asn$^{118}$Ala$^{119}$Tyr$^{120}$Leu$^{121}$ |
| m104 (SEQ ID NO: 80) | Tyr$^{117}$Asn$^{118}$Ala$^{119}$Tyr$^{120}$Gln$^{121}$ |
| m108 (SEQ ID NO: 81) | Phe$^{117}$Asn$^{118}$Ala$^{119}$Ile$^{120}$Trp$^{121}$ |

TABLE 4

| | |
|---|---|
| Wt | Ala$^{117}$Asn$^{118}$Ala$^{119}$Trp$^{120}$Lys$^{121}$ |
| mutein "1" | Ala$^{117}$Asn$^{118}$Ala$^{119}$Trp$^{120}$Lys$^{121}$ |
| m207 (SEQ ID NO: 82) | Thr$^{117}$---$^{118}$---$^{119}$Trp$^{120}$Leu$^{121}$ |
| m212 (SEQ ID NO: 83) | His$^{117}$---$^{118}$---$^{119}$Trp$^{120}$Leu$^{121}$ |
| m202 (SEQ ID NO: 84) | Ile$^{117}$---$^{118}$---$^{119}$Trp$^{120}$Arg$^{121}$ |
| m204 (SEQ ID NO: 85) | His$^{117}$---$^{118}$---$^{119}$Trp$^{120}$Thr$^{121}$ |
| m206 (SEQ ID NO: 86) | Thr$^{117}$---$^{118}$---$^{119}$Trp$^{120}$Arg$^{121}$ |
| m208 (SEQ ID NO: 87) | Ala$^{117}$---$^{118}$---$^{119}$Trp$^{120}$Arg$^{121}$ |
| m203 (SEQ ID NO: 88) | Arg$^{117}$---$^{118}$---$^{119}$Trp$^{120}$Ser$^{121}$ |

TABLE 4-continued

| | |
|---|---|
| m209 (SEQ ID NO: 89) | Asn$^{117}$---$^{118}$---$^{119}$Trp$^{120}$Arg$^{121}$ |
| m200 (SEQ ID NO: 90) | Lys$^{117}$---$^{118}$---$^{119}$Trp$^{120}$Ser$^{121}$ |
| m201 (SEQ ID NO: 91) | Ser$^{117}$---$^{118}$---$^{119}$Val$^{120}$Phe$^{121}$ |
| m211 (SEQ ID NO: 92) | Lys$^{117}$---$^{118}$---$^{119}$Trp$^{120}$Thr$^{121}$ |

TABLE 5

| | |
|---|---|
| Wt | Ala$^{117}$Asn$^{118}$Ala$^{119}$Trp$^{120}$Lys$^{121}$ |
| mutein "1" | Ala$^{117}$Asn$^{118}$Ala$^{119}$Trp$^{120}$Lys$^{121}$ |
| m300 (SEQ ID NO: 93) | Ala$^{117}$---$^{118}$---$^{119}$Trp$^{120}$Tyr$^{121}$ |
| m301 (SEQ ID NO: 94) | His$^{117}$---$^{118}$---$^{119}$Trp$^{120}$Met$^{121}$ |
| m302 (SEQ ID NO: 95) | His$^{117}$---$^{118}$---$^{119}$Trp$^{120}$Tyr$^{121}$ |
| m303 (SEQ ID NO: 96) | Glu$^{117}$---$^{118}$---$^{119}$Trp$^{120}$Tyr$^{121}$ |
| m304 (SEQ ID NO: 97) | Gln$^{117}$---$^{118}$---$^{119}$Trp$^{120}$Tyr$^{121}$ |

As disclosed by Tables 1 to 5, illustrative streptavidin muteins of the invention comprise or have one of the sequences of any of SEQ ID NOs: 21 to 97 at sequence positions 117 to 121 of the amino acid sequence of wild type streptavidin. These streptavidin muteins can either have the wildtype streptavidin sequence at any of the other sequence positions or the sequence of any known streptavidin muteins, for example, the sequence of the known muteins "1" or "2" that comprise the amino acid sequence Val$^{44}$-Thr$^{45}$-Ala$^{46}$-Arg$^{47}$ (SEQ ID NO: 10) or Ile$^{44}$-Gly$^{45}$-Ala$^{46}$-Arg$^{47}$ (SEQ ID NO: 11) at amino acid positions 44 to 47.

In some embodiments, a mutein of the invention comprises at sequence positions 117 to 121 an amino acid sequence of consisting of the group of Glu$^{117}$Asn$^{118}$Ala$^{119}$Trp$^{120}$Phe$^{121}$ (SEQ ID NO: 56)

Asp$^{117}$Asn$^{118}$Ala$^{119}$Gly$^{120}$Tyr$^{121}$ (SEQ ID NO: 57)

Glu$^{117}$Asn$^{118}$Ala$^{119}$Gly$^{120}$Tyr$^{121}$ (SEQ ID NO: 58)

Arg$^{117}$Asn$^{118}$Ala$^{119}$Met$^{120}$Met$^{121}$ (SEQ ID NO: 59)

Arg$^{117}$Asn$^{118}$Ala$^{119}$Gly$^{120}$Phe$^{121}$ (SEQ ID NO: 60)

Ala$^{117}$Asn$^{118}$Ala$^{119}$Pro$^{120}$Ala$^{121}$ (SEQ ID NO: 61)

Ala$^{117}$Asn$^{118}$Ala$^{119}$Met$^{120}$Val$^{121}$ (SEQ ID NO: 62)

Gln$^{117}$Asn$^{118}$Ala$^{119}$Ser$^{120}$Ala$^{121}$ (SEQ ID NO: 63)

Ala$^{117}$Asn$^{118}$Ala$^{119}$Gly$^{120}$Phe$^{121}$ (SEQ ID NO: 64)

Gln$^{117}$Asn$^{118}$Ala$^{119}$Met$^{120}$Val$^{121}$ (SEQ ID NO: 65)
and

His$^{117}$---$^{118}$---$^{119}$Trp$^{120}$Tyr$^{121}$. (SEQ ID NO: 95)

Also such a mutein may comprise, for example, either the wild-type streptavidin sequence, the sequence of mutein "1" or of mutein "2" at any other position (apart from the Cys residue at position 127 that is shared by all muteins of the present invention).

In other illustrative embodiments, the streptavidin muteins of the invention may, in addition to the Cys residue at sequence position 127, comprise or consist of the sequence of any of the following muteins that are shown in FIG. 4 of International Patent Application WO 2014/076277, i.e. the following muteins:
m400, m402, m4001, mutein"1"-m36, mutein"1"-m23, mutein"1"-m41, mutein"1"-m4, mutein"1"-m12, mutein"1"-m22, mutein"1"-m31, mutein"1"-m32, mutein"1"-m35, mutein"1"-m38, mutein"1"-m40, mutein"1"-m42, mutein"1"-m45, mutein"1"-m46, mutein"1"-m47, mutein"1"-m7, mutein"1"-m10, mutein"1"-m17, mutein"1"-m21, mutein"1"-m24, mutein"1"-m27, mutein"1"-m28, mutein"1"-m30, mutein"1"-m33, mutein"1"-m1, mutein"1"-m3, mutein"1"-m8, mutein"1"-m15, mutein"1"-m6, mutein"1"-m9, mutein"1"-m20, mutein"1"-m34, mutein"1"-m14, mutein"1"-m18, mutein"1"-m19, m4001-m8, m4001-m21, m4001-m9, m4001-m1, m4001-m2, m4001-m3, m4001-m5, m4001-m13, m4001-m14, m4001-m24, m4001-m4, m4001-m6, m4001-m7, m4001-m10, m4001-m15, m4001-m23, m4001-m17, m4001-m12, m4001-m20, mutein"1"-m101, mutein"1"-m106, mutein"1"-m111, mutein"1"-m100, mutein"1"-m110, mutein"1"-m104, mutein"1"-m108, mutein"1"-m207, mutein"1"-m212, mutein"1"-m202, mutein"1"-m204, mutein"1"-m206, mutein"1"-m208, mutein"1"-m203, mutein"1"-m209, mutein"1"-m200, mutein"1"-m201, mutein"1"-m211, mutein"1"-m300, mutein"1"-m301, mutein"1"-m302, mutein"1"-m303, mutein"1"-m304 and m1-9.

Turning now to the practical uses of the muteins of the invention (for example, for affinity chromatography under denaturing conditions), it may be desirable to employ a ligand which, due to a higher binding affinity or/and due to being present at higher concentrations than the streptavidin binding peptide, can detach the binding of the streptavidin binding peptide (for example, a Strep-Tag® (II) peptide or a Di-tag peptide as described herein) from the streptavidin mutein according to the invention. Usually this ligand acts as competitor of the Strep-Tag® peptide. This (competitive) ligand is usually present in free form, meaning not fused to any protein or other molecule. In this manner it is possible to release (generally by competitive elution) bound streptavidin binding peptide ligands or proteins to which a streptavidin binding peptide such as the Strep-Tag® (II) peptide or a Di-tag peptide is fused under the chosen, for example, denaturing elution conditions. This is, e.g., important for elution of the bound fusion protein from the streptavidin mutein affinity column or to reverse the binding of multimeric low affinity fusion proteins carrying a streptavidin binding peptide that are multimerized via a backbone of streptavidin mutein (multimers) of the present invention. Hence, in this aspect, the present invention concerns those streptavidin muteins whose binding affinity for peptide ligands is such that they can be competitively eluted by other streptavidin ligands like, e.g., biotin, iminobiotin, lipoic acid, thiobiotin, desthiobiotin, diaminobiotin, HABA (hydroxyazobenzene-benzoic acid) or/and dimethyl-HABA. The use of coloured substances such as HABA or dimethyl-HABA may have the advantage that the elution from a column can be checked visually. However, irrespective of this, the binding affinity of the streptavidin muteins of the present invention for peptide ligands, particularly for Strep-Tag® II is usually higher than that of wt-streptavidin or than that of the muteins "1" or "2" disclosed in U.S. Pat. No. 6,103,493. Therefore, in some embodiments higher affinity ligands like thiobiotin or biotin are preferred for sharp elution. Alternatively, also isolated peptide ligands binding to the biotin binding pocket, e.g. as described herein, may be used for competitive elution. For the sake of completeness, it is noted that the interaction/binding of a streptavidin binding peptide (that is usually fused or conjugated to a protein of interest) to a streptavidin mutein of the invention may not necessarily be disrupted by competitive elution but also by any other means that is able to disrupt this non-covalent complex. For example, if such fusion proteins are immobilized on a surface that is coated with a streptavidin mutein of the invention such as a surface plasmon resonsance chip, an ELISA plate or even a chromatography resin, the binding can be disrupted by change of the pH, for example, by addition of a base such as NaOH. Such an approach might even be preferred for the regeneration of a surface plasmon resonsance chip but also a chromatography resin that has a streptavidin mutein of the invention immobilized thereon.

It may be preferable for certain detection methods to use the streptavidin muteins of the present invention in a labeled form. Accordingly, a further subject matter of this invention is a polypeptide according to the invention which is characterized in that it carries at least one label. Suitable labeling groups are known to a person skilled in the art and comprise the usual radiolabels, fluorescent labels, luminescent labels and chromophore labels as well as substances and enzymes which generate a substance that can be determined in a chemical or enzymatic reaction. In this connection, all labels known for wt-streptavidin can also be coupled to the streptavidin muteins according to the present invention.

A further aspect of the present invention concerns a nucleic acid which comprises a sequence coding for a streptavidin mutein of the present invention. Such a nucleic acid is optionally operatively linked to a sequence coding for a signal peptide and, in a particular embodiment, the sequence coding for the signal peptide is the sequence for the OmpA signal peptide. Moreover, it is also possible to use other signal peptides and this may even be preferable especially depending on the expression system or host cell used. A large number of such signal peptides are known in the state of the art and will not be elucidated in detail here. However, cytoplasmic expression is preferred, i.e. with a start methionine instead of the signal sequence (cf. Schmidt & Skerra, J. Chromatogr. A 676 (1994), 337-345).

A further aspect of the present invention concerns a vector which contains at least one copy of an aforementioned nucleic acid in an operatively functional environment. An operatively functional environment is understood as those elements which enable, favor, facilitate or/and increase the expression, i.e. transcription or/and a subsequent processing, of the mRNA. Examples of such elements are promoters, enhancers, transcription initiation sites and termination sites, translation initiation sites, polyA-sites etc.

The vector is selected depending on the intended expression system and for this single copy plasmids, multi-copy plasmids as well as vehicles which facilitate an integration of the nucleic acid into the host genome come into consideration. A large number of suitable vectors are known from the state of the art and will not be described in detail here. They optionally contain standard elements used for vectors such as resistances, selection markers or/and elements which for example enable an amplification of the nucleic acid or the induction of expression.

A further aspect of the present invention concerns a cell which is transformed or transfected with such a vector which carries as an insert at least one copy of a nucleic acid sequence coding for a streptavidin mutein according to the invention. The selection of the cell is not particularly critical and in general it is possible to use any cells that are suitable for such purposes. Prokaryotic as well as eukaryotic cells and yeasts come into consideration. For practical reasons prokaryotic cells are generally preferred and in particular *E. coli* for the expression of an unglycosylated protein as in the present case.

Yet a further aspect of the present invention concerns a process for the production of a streptavidin mutein according to the invention which is characterized by the following steps:
(a) transforming a suitable host cell with a vector which contains a nucleic acid coding for the streptavidin mutein,
(b) culturing the host cell under conditions in which an expression of the streptavidin mutein takes place,
(c) isolating the polypeptide.

With respect to the production process, streptavidin muteins according to the invention may have a toxic effect due to their ability to bind to endogeneous biotin. Hence, when culturing the host cell the conditions should be selected such that the expression product that forms is either transported from the inside of the host cell used, for example, into the periplasm or into the culture medium by means of a suitable signal sequence or it aggregates inside the cell in the form of insoluble inclusion bodies. In the former case the streptavidin mutein according to the invention can be isolated from the periplasmic cell fraction or the cell supernatant whereas in the latter case, step (c) of the process according to the invention comprises the lysis of host cells, the isolation of the streptavidin mutein in the form of inclusion bodies and the renaturation of the streptavidin mutein. In this case *E. coli* is preferred as the host cell.

The practical applications for the streptavidin muteins or the streptavidin mutein/peptide ligand system according to the invention are essentially the same as those for conventional streptavidin/biotin or streptavidin/peptide ligand systems. However, as explained above, the muteins described here have the advantage that all these practical applications can be carried out in the presence of one or more chaotrope reagents that provide for denaturing conditions. This advantage over the conventional streptavidin/biotin system or over the system as disclosed by U.S. Pat. No. 6,103,493 applies in particular to affinity chromatography and to purification, isolation or determination methods for recombinant proteins.

Accordingly, the invention also concerns the use of a streptavidin mutein according to the invention in a method of isolating, purifying, detecting or immobilizing under denaturing conditions a protein. The protein of interest can be fused with a) a peptide sequence of the formula Trp-Xaa-His-Pro-Gln-Phe-Yaa-Zaa (SEQ ID NO: 8) in which Xaa represents an arbitrary amino acid and Yaa and Zaa either both denote Gly or Yaa denotes Glu and Zaa denotes Arg or Lys. Alternatively, the protein of interest can be fused b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa- (SEQ ID NO: 9) where Oaa is Trp, Lys or Arg, Xaa is any amino acid and where either Yaa and Zaa are both Gly or Yaa is Glu and Zaa is Lys or Arg. Affinity peptides with such a sequential arrangement of at least two streptavidin binding modules are known from International Patent Application WO 02/077018 or U.S. Pat. No. 7,981,632, for example.

In this method of isolating, purifying or detecting, a liquid containing the protein to be isolated or purified is contacted with the optionally immobilized streptavidin mutein under suitable and at the same time denaturing conditions in order to bind the peptide sequence to the streptavidin mutein. Thereafter, the resulting complex is separated from the liquid and the protein is released from the complex or detected. In some embodiments, the peptide sequence is preferably the one of the STREP-TAG®II affinity tag. In other embodiments, the peptide sequence is preferably the di-tag3 sequence (WSHPQFEKGGGSGGGSGGGSWSHPQFEK; SEQ ID NO: 5), the di-tag2 sequence Trp-Ser-His-Pro-Gln-Phe-Glu-Lys-(GlyGlyGlySer)2-Trp-Ser-His-Pro-Gln-Phe-Glu-Lys (SEQ ID NO: 6) that are described in International Patent Application WO02/077018 or U.S. Pat. No. 7,981,632 or the sequence WSHPQFEKGGGSGGGSGGGSAWSHPQFEK (SEQ ID NO: 7, also known as TWIN-STREP-TAG™ (IBA GmbH)). The peptide sequence is preferably fused to the N- or/and C-terminus of the protein. The streptavidin mutein can be bound to a solid phase or can be capable of binding to it.

An advantage of utilizing the streptavidin mutein/peptide ligand system according to the invention in an isolation or purification method is that (apart from the denaturing conditions) very mild conditions can be used to elute the fusion protein carrying the peptide ligand. Hence it is possible to incubate a solid phase coupled to the streptavidin mutein, such as for example an affinity chromatography column to which the fusion protein has been adsorbed, with an adequate concentration of a ligand selected from biotin and derivatives thereof in order to release the fusion protein from the complex again. In this connection, the use of biotin has proven to be particularly advantageous.

The streptavidin muteins according to the invention can be used in detection methods in an essentially similar manner to the corresponding methods that are known for conventional streptavidin. A further application is the qualitative or quantitative determination under denaturing conditions of a protein of interest which may be fused with a) a peptide sequence of the formula Trp-Xaa-His-Pro-Gln-Phe-Yaa-Zaa in which Xaa represents an arbitrary amino acid and Yaa and Zaa either both denote Gly or Yaa denotes Glu and Zaa denotes Arg or Lys. Alternatively, the protein of interest may be fused b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa- (SEQ ID NO: 9) where Oaa is Trp, Lys or Arg, Xaa is any amino acid and where either Yaa and Zaa are both Gly or Yaa is Glu and Zaa is Lys or Arg. In this method the protein to be determined is contacted under denaturing but otherwise suitable conditions with a labeled streptavidin mutein in order to bind the peptide sequence to the streptavidin mutein, is washed and the label is determined. Such a determination method can, for example, be carried out qualitatively to detect proteins in Western blots or quantitatively as in an ELISA. Suitable labels are all known radioactive and non-radio-active labeling groups e.g. luminescent groups, enzymes, metals, metal complexes etc. The streptavidin can be directly labeled e.g. by covalent coupling. However, indirect labels such as labeled anti-streptavidin antibodies or biotinylated enzymes, etc. can also be used.

A further advantageous aspect of the invention is the use of the streptavidin muteins according to the invention to immobilize under denaturing conditions a protein of interest which is fused with a) a peptide sequence Trp-Xaa-His-Pro-Gln-Phe-Yaa-Zaa in which Xaa represents an arbitrary amino acid and Yaa and Zaa either both denote Gly or Yaa denotes Glu and Zaa denotes Arg or Lys. Alternatively, the protein of interest is fused b) with a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa- (SEQ ID NO: 9) where Oaa is Trp, Lys or Arg, Xaa is any amino acid and where either Yaa and Zaa are both Gly or Yaa is Glu and Zaa is Lys or Arg. In one embodiment, the peptide sequence is the sequence (WSHPQFEKGGGSGGGSGGGSWSHPQFEK; SEQ ID NO: 5). In another embodiment, the peptide sequence is the sequence WSHPQFEKGGGSGGGSGGSAWSHPQFEK (SEQ ID NO: 7). This immobilization is preferably carried out on solid phases coated with streptavidin muteins of the invention such as microtitre plates, beads (e.g. made of agarose or other polymers like, e.g., polymethacrylate), microbeads made of organic or paramagnetic materials, nanobeads made of organic or paramagnetic materials or sensor chips such as BIACORE® (Global Life Sciences Solutions USA LLC) chips or other support as e.g. used for lateral flow assays or for making protein arrays The terms "denaturing conditions", "denaturation" and "denaturing" are used herein in accordance with their regular meaning in the field of protein chemistry/protein folding. Accordingly, "denaturation" is used to refer to the process in which proteins lose the quaternary structure, tertiary structure and/or secondary structure which is present in their native state, by exposure to and contact with a chaotropic agent. A chaotropic agent (chaotrope) is a compound that is able to disrupt in aqueous solution the hydrogen bonding network between water molecules (i.e. exerts chaotropic activity). This has an effect on the stability of the native state of proteins that are present in the aqueous solution by weakening the hydrophobic effect. A chaotropic agent reduces, for example, the amount of order in the structure of a protein formed by water molecules, both in the bulk and the hydration shells around hydrophobic amino acids, and may cause its denaturation. Thus, "denaturing conditions" as used herein refer to such conditions in which a chaotropic agent is present in an amount that is able to induce at least partial loss of the folded structure of a protein of interest. Examples of chaotropic agents that can be used in methods of the invention include, but are not limited to urea, thiourea, guanidine hydrochloride, lithium perchlorate, hydroxide ions, and combinations thereof. Illustrative examples of denaturing conditions include the presence of guanidinium chloride in about 2 M to about 6 M (at high concentrations of guanidinium chloride as about 6 M proteins lose their ordered structure, and they tend to become randomly coiled), the presence of urea in about 1 to about 8 M, or the use of a concentrated solution of lithium perchlorate (for example, about 4.5 M). The presence of hydroxide ions, for example, in concentrations of about 0.05 M, or about 1 M, or about 2 M (which is equivalent to a 1N or 2 N NaOH solution) is a further example of denaturing conditions as used in methods of the present invention.

In this context, it is noted that it is also possible to use the streptavidin muteins according to the invention in a conventional streptavidin/biotin (derivative) system. Put differently, this means the use of the streptavidin muteins according to the invention to determine or isolate substances which carry a group capable of binding to streptavidin. If only a part of the wt-streptavidin is replaced by the streptavidin muteins according to the invention, particular effects can be achieved in this connection via the formation of mixed tetramers.

A further aspect of the present invention relates to a solid phase having immobilized thereon a streptavidin mutein as described herein. Illustrative examples of suitable solid phases include a cellulose membrane, a plastic membrane, a biosensor, a lateral flow device or an affinity chromatography matrix. Examples of affinity chromatography matrices include, to mention only a few, a polysaccharide gel, a polyacrylamide gel, an agarose gel, polysaccharide grafted silica, polyvinylpyrrolidone grafted silica, polyethylene oxide grafted silica, poly(2-hydroxyethylaspartamide) silica, poly(N-isopropylacrylamide) grafted silica, a styrene-divinylbenzene gel, a copolymer of an acrylate or an acrylamide and a diol, a co-polymer of a polysaccharide and N,N'-methylenebisacrylamide and a combination of any two or more thereof. Further examples of well-known affinity chromatography matrices (or stationary phases) that are also suitable in the present invention, include derivatized silica or a crosslinked gel. A crosslinked gel (which is typically manufactured in a bead form) may be based on a natural polymer, i.e. on a polymer class that occurs in nature. For example, a natural polymer on which a chromatography stationary phase is based is a polysaccharide. A respective polysaccharide is generally crosslinked. An example of a polysaccharide matrix is an agarose gel (for example, SUPERFLOW™ (Sterogene Bioseparations) agarose or a SEPHAROSE® (GE Healthcare) material such as SUPER-FLOW™ SEPHAROSE® resin that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as SEPHADEX® resin or SUPERDEX® resin, both available from GE Healthcare. Another illustrative example of such a chromatography material is SEPHACRYL® resin which is also available in different bead and pore sizes from GE Healthcare.

Yet a further aspect of the invention concerns a reagent kit that contains a streptavidin mutein according to the invention or a solid phase having immobilized thereon a streptavidin mutein as described herein. The kit may optionally contain standard buffer and auxiliary substances and additives. Such a reagent kit is in particular intended to be used in one of the isolation, purification, assay or determination methods described above. However, the kit is also suitable for other methods in which the conventional streptavidin/biotin system is used e.g. for nucleic acid hybridization assays or immunoassays. The reagent kit can contain the streptavidin mutein according to the invention as free, non-modified protein or/and in a solid phase-bound or/and labeled form.

The invention is further illustrated by the following tables, figures and examples.

BRIEF DESCRIPTION OF THE FIGURES

FIG. 1A shows the full length amino acid sequence of mature wild-type streptavidin (residues 1 to 159; SEQ ID NO: 1), while FIG. 1B shows the amino acid sequence of a shortened version of mature wild-type streptavidin (residues 14 to 139; SEQ ID NO: 2) that was used in the present invention for the generation of inventive muteins.

FIG. 2 shows three sequence motives of muteins of the invention having at least one mutation within the peptide segment of residues 117 to 121 of the streptavidin sequence. Preferred residues are shown in bold print, less preferred residues are shown in normal print. Amino acid residues shall be considered position wise and each may be in principle combined with any other occurring at another position. Sequence motif 1 is characterized in that glycine is highly preferred at position 120 and may be combined with a large hydrophobic residue, preferably tyrosine or phenylalanine, or, less preferably, methionine at position 121 and a charged, preferably glutamate, aspartate, arginine or histidine, or, less preferably, a hydrophilic residue like glutamine, asparagine, serine or threonine or a hydrophobic residue like leucine or methionine at position 117. Sequence motif 2 is characterized in that a large hydrophobic residue, preferably tyrosine or phenylalanine but not tryptophane is highly preferred at position 120 instead of small glycine while leucine, isoleucine or methionine are less preferred at this position 120. Then also hydrophobic residues are preferred at positions 117 and 121, whereby aromatic tyrosine or phenylalanine are preferred for position 117 and large but non-aromatic hydrophobic residues, most preferably leucine, isoleucine and methionine, are preferred for position 121. Less preferred for position 117 are the residues arginine, tryptophane or glutamine and for position 121 the residues glutamine, glycine, tryptophane, serine, alanine or valine. Sequence motif 3 is characterized in that amino acids at positions 118 and 119 are deleted. In this case, tryptophane at original position 120 is strongly preferred and valine is less preferred and these residues may be combined with preferably tyrosine at position 121, whereby also other residues like leucine, methionine, threonine, serine, phenylalanine or arginine may occur at position 121, and with most preferably a hydrogen bond acceptor and/or donator like histidine, gltuamine or glutamate or, less preferably also other residues like threonine, arginine, asparagine, lysine, serine, alanine or isoleucine at position 117.

FIG. 3 shows the amino acid sequence of all muteins experimentally generated and characterised herein (muteins m302 (SEQ ID NO: 13), m302C (SEQ ID NO: 14), m1-9 (SEQ ID NO: 15), and m1-9C (SEQ ID NO: 16)), aligned with the amino acid sequence of amino acid positions 14 to 139 of wild type streptavidin (SEQ ID NO: 2) and of mutein "1" (SEQ ID NO: 12) described in U.S. Pat. No. 6,103,493 (that is commercially available under its trademark "StrepTactin®. When the muteins were produced by *E. coli* in the cytosol as inclusion bodies for subsequent refolding, purification and analysis, the resulting protein sequences were produced as shown with an additional methionine at the N-terminal end (position 13, not shown in FIG. 4). Deleted amino acids in the muteins m302 and m302C are indicated by a dash (-). For these two muteins, amino acid numbering has been conducted in a manner maintaining comparability at equivalent positions. It should, however, be noted that the muteins m302 and m302C in which the amino acid residues at sequence positions 118 and 119 are deleted, are with 125 amino acid residues two amino acids shorter than mutein "1" and the muteins m1-9 and m1-9C (who have a length of 127 amino acid residues). In the muteins of the invention (m302C and m1-9C) the Cys residue at sequence position 127 is underlined and depicted in bold. In addition, the mutated amino acids in the region of sequence positions 117 to 121 in the muteins m302, m302C, m1-9, and m1-9C are in bold print.

FIG. 6 shows the melting temperature curves for wild-type streptavidin (wt-strep, SEQ ID NO: 2), streptavidin mutein "1" (SEQ ID NO: 12), streptavidin mutein m1-9 (SEQ ID NO: 15) and streptavidin mutein m1-9C (SEQ ID NO: 16).

EXAMPLES

General Methods

DNA manipulations were carried out by conventional genetic engineering methods (see e.g. Sambrook et al., Molecular Cloning. A Laboratory Manual (1989), Cold Spring Harbor Press), *E. coli* K12 TOP10 (Life Technologies) for cloning and *E. coli* BL21 for expression of the feline immunodeficiency virus Gag protein (FIV GAG) fused to the streptavidin peptide Trp-Ser-His-Pro-Gln-Phe-Glu-Lys-(GlyGlyGlySer)2-Gly-Gly-Ser-Ala-Trp-Ser-His-Pro-Gln-Phe-Glu-Lys (SEQ ID NO: 7) under formation of inclusion bodies. Cytosolic expression of the streptavidin muteins for subsequent protein isolation for coupling to SEPHAROSE® resin was carried out according to Schmidt & Skerra, J. Chromatogr. A 676 (1994), 337-345). Sequencings were carried out according to the standard dideoxy technique by Sequence Laboratories Gottingen GmbH. Primers and oligonucleotides were synthesized using an Applied Biosystems Expedite DNA synthesizer Example 1: Mutagenesis/Generation of Expression Vectors Encoding Muteins m302C and m1-9

The expression vectors encoding the muteins m302C and m1-9C were generated by site specific mutagenesis starting from the expression vector of the parental muteins m302 and m1-9, respectively (see International Patent Application WO 2014/076277, Example 8 for a description of the pASK75 based expression vector for the muteins m302 and m1-9). The codon for the mutation His 127->Cys was introduced via the primers that were used for amplification of the expression vector. These two primers having opposite directions for amplification were annealed to the expression vector and then the expression vector was amplified by PCR.

Example 2: Production of Streptavidin Muteins on a Preparative Scale

The streptavidin muteins "1" (SEQ ID NO: 12), m1-9 (SEQ ID NO: 15) and m302 (SEQ ID NO: 13) were produced as described, for example, in International Patent Application WO 2014/076277. The known expression system for recombinant minimal streptavidin (Schmidt and Skerra (1994), supra) was also used to produce the streptavidin muteins m1-9C (SEQ ID NO: 16) and m302C (SEQ ID NO: 14) on a preparative scale. For this the major part of the coding region was removed from the vector pSA1 which contains the coding region of wt-streptavidin and the T7 promoter by using the singular SacII and HindIII restriction sites and replaced by the corresponding regions from the mutated pASK-IBA2-SAm1 plasmids. wt-streptavidin and the streptavidin muteins were subsequently expressed in the form of cytoplasmic inclusion bodies, solubilized, renatured and purified by fractional ammonium sulphate precipitation as described by Schmidt and Skerra (1994) supra. The purity of the obtained streptavidin muteins was checked with an Agilent 2100 Bioanalyzer.

Figure 4:
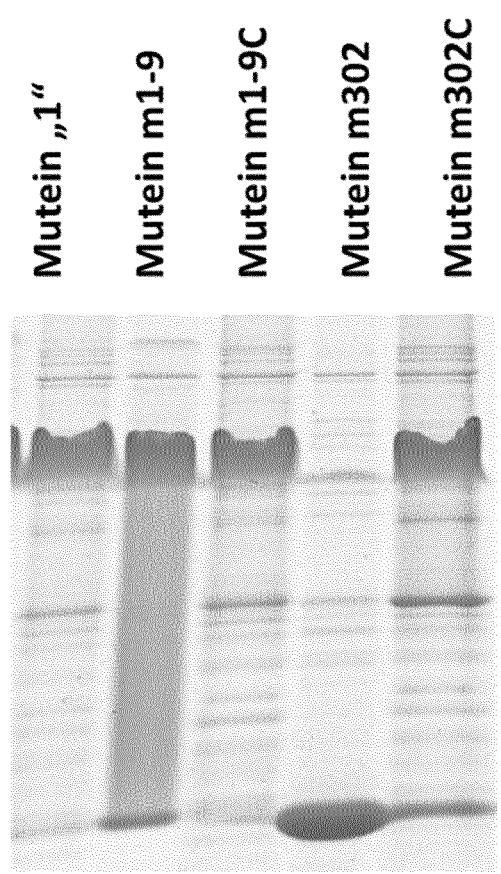
FIG. 4 shows a SDS-polyacrylamide gel electrophoresis (PAGE) analysis of the stability of the muteins m302, m302C, m1-9, and m1-9C in comparison to mutein "1". The samples for the SDS-PAGE were not boiled prior to loading onto the gel in order to be able to determine the influence of the denaturing effect of the SDS (detergent) on the streptavidin muteins. The SDS-PAGE was conducted under non-reducing conditions.

Example 3: Analysis of the Stability of Streptavidin Muteins Under Denaturing Conditions In order to determine the stability of the streptavidin muteins SDS-PAGE analysis was carried out. The samples of the muteins for the SDS-PAGE were not boiled prior to loading onto the gel in order to be able to determine the influence of the denaturing effect of the SDS (detergent) on the streptavidin muteins. The SDS-PAGE was conducted under non-reducing conditions and the gel was stained with Coomassie Brilliant Blue. FIG. 4 shows the result of the SDS-PAGE, comparing the stability of the muteins m302, m302C, m1-9, and m1-9C to mutein "1" under these denaturing conditions.

Notably, as evident from the single prominent band in the lane of mutein "1", the tetrameric form of this mutein remains intact even in the presence of SDS, indicating that the mutein "1" is very stable under denaturing conditions. In contrast to this, the mutein m1-9 is far less stable, as evident from the band of the monomeric subunits in the SDS-PAGE extended degree of instability. The instability is even much more pronounced for the mutein m302. This mutein completely dissociates into its monomers under the denaturing conditions of the SDS page. As also evident from FIG. 4, the introduction of the Cys residue at position 127 greatly increases the stability of the muteins m1-9 and m302 under these conditions. The mutein m1-9C seems to be present only in its tetrameric form. Under these conditions, the relative gain in stabilization seems to be even more pronounced for the mutein 302. The mutein m302C seems to be able to maintain its tetrameric structure to a large extent, only a small fraction of this streptavidin mutein dissociates into its monomer under these denaturing conditions.

Example 4: Production of Fusion Protein and Purification of the Fusion Protein from Inclusion Bodies Via Affinity Chromatography Under Denaturing Conditions The streptavidin muteins m1-9 (SEQ ID NO: 15) and m1-9C (SEQ ID NO: 16) as well as streptavidin mutein "1" (SEQ ID NO: 12) of U.S. Pat. No. 6,103,493 were prepared as described in Example 3 of the present application as well as in Example 9 of International Patent Application WO 2014/076277. Then, the streptavidin muteins were coupled to NHS-activated SEPHAROSE® 4 Fast Flow resin (GE Healthcare) according to the instructions of the manufacturer (cf. Schmidt and Skerra, 1994, supra). Sepharose gel loading (SUPERFLOW™) with the respective streptavidin mutein was determined with a PIERCE™ BCA assay (Thermo Fisher Scientific) according to the instructions of the manufacturer and as described in International Patent Application WO 2014/076277.

In order to examine the behaviour of these two streptavidin muteins and the streptavidin mutein "1" of U.S. Pat. No. 6,103,493 immobilized in this manner in the affinity purification of STREP-TAG® II affinity tag-carrying fusion proteins under denaturing conditions, the recombinant feline immunodeficiency virus Gag protein fused to the streptavidin peptide Trp-Ser-His-Pro-Gln-Phe-Glu-Lys-(GlyGlyGly-Ser)2-Gly-Gly-Ser-Ala-Trp-Ser-His-Pro-Gln-Phe-Glu-Lys (SEQ ID NO: 7, also known under its trademark "TWIN-STREP-TAG™") was expressed using the expression vector pASG-103 (IBA GmbH, catalogue number 5-4103-001) in E. coli BL 21. Use of this expression vector leads to the formation of inclusion bodies of the FIV GAG protein in the cytosol of E. coli. BL21.

The recombinant protein expression and cell harvest was carried out in accordance with the following protocol. Transformed E. coli BL21 cells were cultured in LB medium containing ampicillin and induced when reaching a sufficient OD. The cell pellet was harvested by centrifugation and resuspended in Buffer W (100 mM Tris-Cl pH8, 150 mM NaCl, 1 mM EDTA). The cells were then disrupted by ultra-sonication in Buffer W followed by centrifugation. The pellet was lysed in Buffer W (at a weight of 100 mg/ml buffer) containing 8 M urea or 6 M guanidine hydrochloride by stirring for 15-60 minutes at room temperature. The sample was adjusted to concentrations of 4 M, 6 M urea, 4 M and 6 M guanidine hydrochloride by dilution with Buffer W, followed by centrifugation. The supernatant was then applied on a 1 ml column of mutein "1" (i.e. a commercially available STREP-TACTIN® column) and of mutant m1-9 and m1-9C, respectively. As mentioned above, in each case, SUPERFLOW® resin was used as affinity chromatography resin to which the respective streptavidin mutein was coupled. The columns had been equilibrated with Buffer W and the appropriate urea or guanidine hydrochloride concentrations of the sample. For experiments with a concentration of 4 M urea and 4 M guanidine, respectively, 2 ml of the sample containing the fusion protein were applied on the column. For experiments with a concentration of 6 M urea and 6 M guanidine, respectively, 3 ml of the sample containing the fusion protein were applied to provide equal amounts of protein. Columns were washed with one column volume (CV) Buffer W+urea/guanidine per wash step until the A280 nm of the flowthrough was below 0.1 or reached a constant signal. The elution was carried out by consecutively applying 0.8, 1.4 and 0.8 CV of Buffer W+50 mM biotin and urea/guanidine to the columns of the employed streptavidin mutein.

Figure 5:
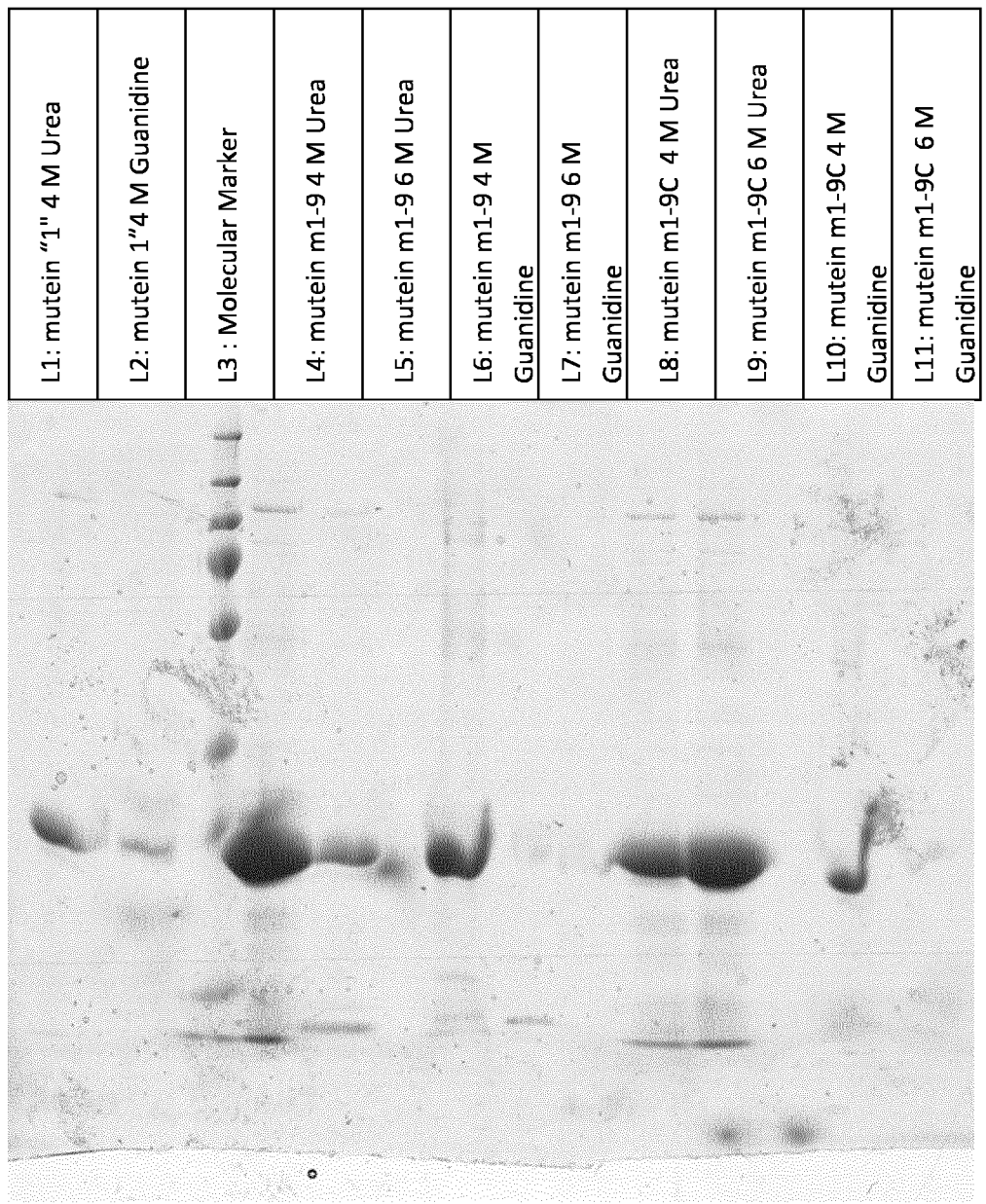
FIG. 5 shows a SDS-PAGE gel analysis of the efficiency of the purification of the feline immunodeficiency virus Gag protein (FIV GAG) to which the streptavidin peptide Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys (SEQ ID NO: 110) was fused C-terminally by affinity chromatography under denaturing conditions. The SDS-PAGE analysis of FIG. 5 shows the comparison of the affinity chromatography using the inventive streptavidin mutein m1-9C with the muteins "1" and m1-9. In more detail, lane 1 shows the eluate of the purification using mutein "1" as affinity reagent in the presence of 4 M urea,
lane 2 shows the eluate of the purification using mutein "1" as affinity reagent in the presence of 4 M guanidinium hydrochloride,
lane 3 shows the molecular marker,
lane 4 shows the eluate of the purification using mutein m1-9 as affinity reagent in the presence of 4 M urea,
lane 5 shows the eluate of the purification using mutein m1-9 as affinity reagent in the presence of 6 M urea,
lane 6 shows the eluate of the purification using mutein m1-9 as affinity reagent in the presence of 4 M guanidinium hydrochloride,
lane 7 shows the eluate of the purification using mutein m1-9 as affinity reagent in the presence of 6 M guanidinium hydrochloride,
lane 8 shows the eluate of the purification using mutein m1-9C as affinity reagent in the presence of 4 M urea,
lane 9 shows the eluate of the purification using mutein m1-9C as affinity reagent in the presence of 6 M urea,
lane 10 shows the eluate of the purification using mutein m1-9C as affinity reagent in the presence of 4 M guanidinium hydrochloride,
lane 11 shows the eluate of the purification using mutein m1-9C as affinity reagent in the presence of 6 M guanidinium hydrochloride.

The effectiveness of the affinity purification was analysed by SDS-PAGE. FIG. 5 shows the comparison of the affinity chromatography using the inventive streptavidin mutein m1-9C with the muteins "1" and m1-9. While protein purity was high in all experiments, no resin allowed the purification of the feline immunodeficiency virus Gag protein at a concentration of 6 M guanidine hydrochloride. As can be taken from FIG. 5, only small amount of protein in 4 M urea containing Buffer W was purified with mutein "1" (STREP-TACTIN® resin), while purification using mutein m1-9 was successful under denaturing conditions with 4 M urea and 6 M urea. It is noted here that for mutein m1-9 using 6 M urea the gel of FIG. 5 shows a band of lower protein concentration. However, later results showed that there is no difference between 4 M and 6 M urea. In addition, it was observed for mutein m1-9 that it can be used for affinity purification using 4 M guanidine but more fusion protein was eluted when urea was used as denaturant. For the mutein m1-9C it was found that its use as affinity material for the purification resulted in an eluate that showed high protein concentration, when 4 M or 6 M Urea was used.

In addition to the SDS-PAGE analysis, it was tested using 1 mM HABA or 10 mM NaOH whether the resins can be appropriately regenerated. When so doing, the following observation was made.

The resin of the STREP-TACTIN® mutein "1" could be successfully regenerated using buffer R (100 mM Tris-Cl pH8, 150 mM NaCl, 1 mM EDTA, 1 mM HABA) after being subjected to purification under denaturing conditions both with urea and guanidine. The resin of the mutein m1-9 could be successfully regenerated using 10 mM NaOH after urea purification but was destroyed in the course of the guanidine purification, while the resin of the mutein m1-9C could be successfully regenerated using 10 mM NaOH after purification using either urea or guanidine as chaotrope. In addition, it was found that resins of the mutein m1-9C can be regenerated using NaOH in concentrations of up to 500 mM while resins of the mutein m1-C were destroyed with NaOH concentrations higher than 100 mM.

The conclusion of these experiments can be summarized as follows. The mutein "1" (also known as STREP-TACTIN®) is not suited for the purification of proteins under denatured conditions. While the mutein m1-9 could be used for purification with 4 M and 6M urea, this mutein is not suited for purification when the denaturing buffer contains guanidine since guanidine destroys the mutein m1-9. As guanidine is a widely used denaturant for purification of proteins from inclusion bodies, the practical use of mutein m1-9 is therefore severly limited. In contrast to this, the mutein m1-9C was successfully used for the purification of the FIV GAG fusion protein when either 4 M or 6 M urea and also 4 M guanidine chloride was used as chaotrope. In addition, the mutein m1-9C was found to be stable against exposure to guanidine and allows the regeneration and reuse of the resin material. Accordingly, in case a protein is to be purified under denatured conditions and a broad range of denaturing conditions including high concentrations of ureas and guanidine is needed, the mutein m1-9C is the molecule of choice. In addition, due to the stability of resins of the mutein m1-9C to NaOH concentrations of up to 500 mM, resins of mutein m1-9C can be advantageously used for affinity purification of proteins in commercial settings that require cleaning-in-place (CIP) protocols for removal of impurifications, as 500 mM NaOH has been found to be a very effective CIP reagent. Thus, due to its high affinity for affinity peptides containing streptavidin binding sequences such as the STREP-TAG® peptide sequence, mutant m1-9C enables now very efficient purification of commercial fusion proteins under physiological and/or denaturing conditions using efficient CIP thereby contributing to improved safety for the use of said fusion proteins.

Example 5: Determination of the Melting Temperature (Tm) of the Streptavidin Muteins The melting temperature was determined under physiological conditions for wild-type core streptavidin (SEQ ID NO: 2, available from IBA GmbH under catalogue number 02-20203) streptavidin muteins "1" (SEQ ID NO: 12), m1-9 (SEQ ID NO: 15) and m1-9C (SEQ ID NO: 16) in order to assess their thermal stability, using the Thermofluor based assay described by Boivin et al. Protein Expression and Purification 91 (2013) 192-206. In more detail, the measurements were carried in Buffer W (100 mM Tris-Cl pH 8, 150 mM NaCl, 1 mM EDTA) with a total sample volume of 25 µl. SYPRO™ orange was used as thermofluor, with the sample containing 2 µl SYPRO™ orange (this solution was prepared by pre-diluting 5000x SYPRO™ orange stock solution gel stain S5692-50 UL (Sigma) to a concentration of 62x to yield a final concentration of 5x SYPRO™ orange in the sample). The protein concentration was 5 µM. For the measurements, the samples were pipetted into a 96 well RT-PCR plate and the wells were sealed with transparent film. The thermocycler was then started, using a heating rate of 1 C°/min and the increase of the fluorescence over time was monitored.

Using this method, the following melting temperatures were obtained (see also FIG. 6 that shows the melting curves of the respective protein):

TABLE 6

| Mutein | Melting Temperature (Tm) (° C.) |
|---|---|
| wt-streptavidin (amino acids 14 to 139) | 75 |
| mutein "1" | 75 |
| m1-9 | 51 |
| m1-9C | 75 | melting points of muteins

As evident from Table 6 the mutein '1' has the same melting temperature of 75° C. as wild-type streptavidin and is thus significantly more thermostable than the mutein m1-9. However, and in contrast to the mutein "1", despite its significantly lower thermostability, the mutein m1-9 is suitable for being used in affinity purification of proteins under denaturing conditions (see Example 4 above). This finding is more than surprising since Reznik et al, Nat Biotechnol. 1996 supra, found a high correlation for streptavidin of biotin binding ability with thermal stability, suggesting that maintenance of the tetrameric structure is essential for streptavidin to maintain its biotin-binding ability and thus also for the ability of streptavidin muteins to maintain their binding ability for streptavidin binding peptides that competitively bind biotin. Rather, in light of the melting temperature of only 51° C., the person skilled in the art would have expected that the mutein m1-9 is not suitable at all for affinity purification of proteins under denaturing conditions. The person skilled in the art would also not have expected that the introduction of a Cys residue at position 127 of the sequence of streptavidin as in mutein m1-9C will improve the stability to the level of the initial mutant "1" or of wild-type streptavidin while maintaining the ability, for example, of the mutein m1-9 for affinity purification of proteins under denaturing conditions.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of certain embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied herein may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

List of amino acid sequences disclosed in the present application:

```
SEQ ID NO: 1 amino acid sequence of mature wild-type streptavidin (residues 1 to 159)

SEQ ID NO: 2 amino acid sequence of mature wild-type streptavidin (residues 14 to 139)

SEQ ID NO: 3 Trp-Ser-His-Pro-Gln-Phe-Glu-Lys, Strep-tag ® II affinity tag

SEQ ID NO: 4 Trp-Arg-His-Pro-Gln-Phe-Gly-Gly, Strap-tag ® affinity tag

SEQ ID NO: 5 Trp-Ser-His-Pro-Gln-Phe-Glu-Lys-(GlyGlyGlySer)₃-Trp-Ser-His-Pro-Gln-Phe-Glu-
Lys, di-tag3 sequence SEQ ID NO: 6 Trp-Ser-His-Pro-Gln-Phe-Glu-Lys-(GlyGlyGlySer)₂-Trp-Ser-His-Pro-Gln-Phe-Glu-
Lys, di-tag2 sequence SEQ ID NO: 7 Trp-Ser-His-Pro-Gln-Phe-Glu-Lys-(GlyGlyGlySer)₂-Gly-Gly-Ser-Ala-Trp-Ser-His-
Pro-Gln-Phe-Glu-Lys, Twin-Strap-tag ®

SEQ ID NO: 8 Trp-Xaa-His-Pro-Gln-Phe-Yaa-Zaa in which Xaa represents an arbitrary amino
acid and Yaa and Zaa either both denote Gly or Yaa denotes Glu and Zaa denotes Arg or Lys SEQ ID NO: 9 Oaa-Xaa-His-Pro-Gln-Phe-Yaa-Zaa-where Oaa is Trp, Lys or Arg, Xaa is any
amino acid and where either Yaa and Zaa are both Gly or Yaa is Glu and Zaa is Lys or Arg SEQ ID NO: 10 Val⁴⁴-Thr⁴⁵-Ala⁴⁶-Arg⁴⁷

SEQ ID NO: 11 Ile⁴⁴-Gly⁴⁵-Ala⁴⁶-Arg⁴⁷

SEQ ID NO: 12: Mutein "1"

SEQ ID NO: 13: Mutein m302

SEQ ID NO: 14: Mutein m302C

SEQ ID NO: 15: Mutein m1-9

SEQ ID NO: 16: Mutein m1-9C
```

-continued

SEQ ID NO: 17  Thr-Thr-Glu-Asp-Asn-Ala-Trp-Lys (TTEANAWK)

SEQ ID NO: 18  HPYFYAPELLFFAK

SEQ ID NO: 19  EGGKETLTPSELRDLV

SEQ ID NO: 20  Ala$^{117}$Asn$^{118}$Ala$^{119}$Trp$^{120}$Lys$^{121}$ (wild type streptavidin)

| SEQ ID NO: 21 | m36 | Tyr$^{117}$Asn$^{118}$Ala$^{119}$Phe$^{120}$Met$^{121}$<br>is: YNAFM |
| --- | --- | --- |
| SEQ ID NO: 22 | m23 | Tyr$^{117}$Asn$^{118}$Ala$^{119}$Tyr$^{120}$Ala$^{121}$<br>is: YNAYA |
| SEQ ID NO: 23 | m41 | Ala$^{117}$---$^{118}$---$^{119}$Trp$^{12}$Tyr$^{121}$<br>is: AXXWY |
| SEQ ID NO: 24 | m4 | Asp$^{117}$Asn$^{118}$Ala$^{119}$Gly$^{120}$Phe1$^{21}$<br>is: DNAGF |
| SEQ ID NO: 25 | m12 | Arg$^{117}$Asn$^{118}$Ala$^{119}$Gly$^{120}$Phe$^{121}$<br>is: RNAGF |
| SEQ ID NO: 26 | m22 | Gln$^{117}$Asn$^{118}$Ala$^{119}$Gly$^{120}$Phe$^{121}$<br>is: QNAGF |
| SEQ ID NO: 27 | m31 | Phe$^{117}$Asn$^{118}$Ala$^{119}$Ser$^{120}$Trp$^{121}$<br>is: FNASW |
| SEQ ID NO: 28 | m32 | Asp$^{117}$Asn$^{118}$Ala$^{119}$Val$^{120}$Met$^{121}$<br>is: DNAVM |
| SEQ ID NO: 29 | m35 | Asp$^{117}$---$^{118}$---$^{119}$Trp$^{120}$Met$^{121}$<br>is: AXXWM |
| SEQ ID NO: 30 | m38 | Glu$^{117}$Asn$^{118}$Ala$^{119}$Gly$^{120}$Phe$^{121}$<br>is: ENAGF |
| SEQ ID NO: 31 | m40 | Tyr$^{117}$Asn$^{118}$Ala$^{119}$Tyr$^{120}$Ser$^{121}$<br>is: YNAYS |
| SEQ ID NO: 32 | m42 | Phe$^{117}$Asn$^{118}$Ala$^{119}$Tyr$^{120}$Gly$^{121}$<br>is: FNAYG |
| SEQ ID NO: 33 | m45 | Tyr$^{117}$Asn$^{118}$Ala$^{119}$Tyr$^{120}$Phe$^{121}$<br>is: YNAGF |
| SEQ ID NO: 34 | m46 | Arg$^{117}$Asn$^{118}$Ala$^{119}$Tyr$^{120}$Ala$^{121}$<br>is: RNAYA |
| SEQ ID NO: 35 | m47 | Tyr$^{117}$Asn$^{118}$Ala$^{119}$Tyr$^{120}$Gly$^{121}$<br>is: WNAYG |
| SEQ ID NO: 36 | m7 | Leu$^{117}$Asn$^{118}$Ala$^{119}$Gly$^{120}$Phe$^{121}$<br>is: LNAGF |
| SEQ ID NO: 37 | m10 | His$^{117}$Asn$^{118}$Ala$^{119}$Gly$^{120}$Tyr$^{121}$<br>is: HNAGY |
| SEQ ID NO: 38 | m17 | Met$^{117}$Asn$^{118}$Ala$^{119}$Gly$^{120}$Phe$^{121}$<br>is: MNAGF |
| SEQ ID NO: 39 | m21 | Arg$^{117}$Asn$^{118}$Ala$^{119}$Gly$^{120}$Tyr$^{121}$<br>is: RNAGY |
| SEQ ID NO: 40 | m24 | Glu$^{117}$Asn$^{118}$Ala$^{119}$Gly$^{120}$Trp$^{121}$<br>is: ENAGW |
| SEQ ID NO: 41 | m27 | His$^{117}$Asn$^{118}$Ala$^{119}$Gly$^{120}$Phe$^{121}$<br>is: HNAGF |
| SEQ ID NO: 42 | m28 | Ser$^{117}$Asn$^{118}$Ala$^{119}$Gly$^{120}$Phe$^{121}$<br>is: SNAGF |
| SEQ ID NO: 43 | m30 | Thr$^{117}$Asn$^{118}$Ala$^{119}$Gly$^{120}$Phe$^{121}$<br>is: TNAGF |

-continued

| | | |
|---|---|---|
| SEQ ID NO: 44 | m33 | Asn$^{117}$Asn$^{118}$Ala$^{119}$Gly$^{120}$Phe$^{121}$<br>is: NNAGF |
| SEQ ID NO: 45 | m1 | Glu$^{117}$Asn$^{118}$Ala$^{119}$Gly$^{120}$Met$^{121}$<br>is: ENAGM |
| SEQ ID NO: 46 | m3 | Trp$^{117}$Asn$^{118}$Ala$^{119}$Cys$^{120}$Cys$^{121}$<br>is: WNACC |
| SEQ ID NO: 47 | m8 | Met$^{117}$Asn$^{118}$Ala$^{119}$Phe$^{120}$Val$^{121}$<br>is: MNAFV |
| SEQ ID NO: 48 | m15 | Ala$^{117}$Asn$^{118}$Ala$^{119}$Asp$^{120}$Trp$^{121}$<br>is: ANADW |
| SEQ ID NO: 49 | m6 | Ser$^{117}$Asn$^{118}$Ala$^{119}$Met$^{120}$Met$^{121}$<br>is: SNAMM |
| SEQ ID NO: 50 | m9 | Arg$^{117}$Asn$^{118}$Ala$^{119}$Val$^{120}$Val$^{121}$<br>is: RNAVV |
| SEQ ID NO: 51 | m20 | Ser$^{117}$Asn$^{118}$Ala$^{119}$Ser$^{120}$Phe$^{121}$<br>is: SNASF |
| SEQ ID NO: 52 | m34 | Ala$^{117}$---$^{118}$---$^{119}$Trp$^{120}$Asp$^{121}$<br>is: AXXWD |
| SEQ ID NO: 53 | m14 | Arg$^{117}$Asn$^{118}$Ala$^{119}$Arg$^{120}$Ala$^{121}$<br>is: RNARA |
| SEQ ID NO: 54 | m18 | Ser$^{117}$Asn$^{118}$Ala$^{119}$Ala$^{120}$Phe$^{121}$<br>is: SNAAF |
| SEQ ID NO: 55 | m19 | Gly$^{117}$Asn$^{118}$Ala$^{119}$Met$^{120}$Met$^{121}$<br>is: GNAMM |
| SEQ ID NO: 56 | m8 | Glu$^{117}$Asn$^{118}$Ala$^{119}$Gly$^{120}$Phe$^{121}$<br>is: ENAGF |
| SEQ ID NO: 57 | m21 | Asp$^{117}$Asn$^{118}$Ala$^{119}$Gly$^{120}$Tyr$^{121}$<br>is: DNAGY |
| SEQ ID NO: 58 | m9 | Glu$^{117}$Asn$^{118}$Ala$^{119}$Gly$^{120}$Tyr$^{121}$<br>is: ENAGY |
| SEQ ID NO: 59 | m1 | Arg$^{117}$Asn$^{118}$Ala$^{119}$Met$^{120}$Met$^{121}$<br>is: RNAMM |
| SEQ ID NO: 60 | m2 | Arg$^{117}$Asn$^{118}$Ala$^{119}$Gly$^{120}$Phe$^{121}$<br>is: RNAGF |
| SEQ ID NO: 61 | m3 | Ala$^{117}$Asn$^{118}$Ala$^{119}$Ala$^{120}$Met$^{121}$<br>is: ANAPA |
| SEQ ID NO: 62 | m5 | Ala$^{117}$Asn$^{118}$Ala$^{119}$Met$^{120}$Val$^{121}$<br>is: ANAMV |
| SEQ ID NO: 63 | m13 | Gln$^{117}$Asn$^{118}$Ala$^{119}$Ser$^{120}$Ala$^{121}$<br>is: QNASA |
| SEQ ID NO: 64 | m14 | Ala$^{117}$Asn$^{118}$Ala$^{119}$Gly$^{120}$Phe$^{121}$<br>is: ANAGF |
| SEQ ID NO: 65 | m24 | Gln$^{117}$Asn$^{118}$Ala$^{119}$Met$^{120}$Val$^{121}$<br>is: QNAMV |
| SEQ ID NO: 66 | m4 | Asn$^{117}$Asn$^{118}$Ala$^{119}$Gly$^{120}$Tyr$^{121}$<br>is: NNAGY |
| SEQ ID NO: 67 | m6 | Ala$^{117}$Asn$^{118}$Ala$^{119}$Ala$^{120}$Val$^{121}$<br>is: ANAAV |
| SEQ ID NO: 68 | m7 | Ser$^{117}$Asn$^{118}$Ala$^{119}$Met$^{120}$Ile$^{121}$<br>is: SNAMI |
| SEQ ID NO: 69 | m10 | His$^{117}$Asn$^{118}$Ala$^{119}$Gly$^{120}$Tyr$^{121}$<br>is: HNAGY |

| | | | |
|---|---|---|---|
| SEQ ID NO: 70 | m15 | Ser$^{117}$Asn$^{118}$Ala$^{119}$Met$^{120}$Ala$^{121}$ is: SNAMA | |
| SEQ ID NO: 71 | m23 | Gln$^{117}$Asn$^{118}$Ala$^{119}$Val$^{120}$Ala$^{121}$ is: QNAVA | |
| SEQ ID NO: 72 | m17 | Tyr$^{117}$Asn$^{118}$Ala$^{119}$Tyr$^{120}$Met$^{121}$ is: YNAYM | |
| SEQ ID NO: 73 | m12 | Leu$^{117}$Asn$^{118}$Ala$^{119}$Trp$^{120}$Gly$^{121}$ is: LNAWG | |
| SEQ ID NO: 74 | m20 | His$^{117}$Asn$^{118}$Ala$^{119}$Ser$^{120}$Met$^{121}$ is: HNASM | |
| SEQ ID NO: 75 | m101 | Tyr$^{117}$Asn$^{118}$Ala$^{119}$Phe$^{120}$Leu$^{121}$ is: YNAFL | |
| SEQ ID NO: 76 | m106 | Phe$^{117}$Asn$^{118}$Ala$^{119}$Phe$^{120}$Leu$^{121}$ is: FNAFL | |
| SEQ ID NO: 77 | m111 | Tyr$^{117}$Asn$^{118}$Ala$^{119}$Leu$^{120}$Trp$^{121}$ is: YNALW | |
| SEQ ID NO: 78 | m100 | Phe$^{117}$Asn$^{118}$Ala$^{119}$Tyr$^{120}$Ile$^{121}$ is: FNAYI | |
| SEQ ID NO: 79 | m110 | Tyr$^{117}$Asn$^{118}$Ala$^{119}$Tyr$^{120}$Leu$^{121}$ is: YNAYL | |
| SEQ ID NO: 80 | m104 | Tyr$^{117}$Asn$^{118}$Ala$^{119}$Tyr$^{120}$Gln$^{121}$ is: YNAYQ | |
| SEQ ID NO: 81 | m108 | Phe$^{117}$Asn$^{118}$Ala$^{119}$Ile$^{120}$Trp$^{121}$ is: FNAIW | |
| SEQ ID NO: 82 | m207 | Thr$^{117}$Asn$^{118}$Ala$^{119}$Trp$^{120}$Leu$^{121}$ is: TXXWL | |
| SEQ ID NO: 83 | m212 | His$^{117}$Asn$^{118}$Ala$^{119}$Trp$^{120}$Leu$^{121}$ is: HXXWL | |
| SEQ ID NO: 84 | m202 | Ile$^{117}$---$^{118}$---$^{119}$Trp$^{120}$Arg$^{121}$ is: IXXWR | |
| SEQ ID NO: 85 | m204 | His$^{117}$Asn$^{118}$Ala$^{119}$Trp$^{120}$Thr$^{121}$ is: HXXWT | |
| SEQ ID NO: 86 | m206 | Thr$^{117}$---$^{118}$---$^{119}$Trp$^{120}$Arg$^{121}$ is: TXXWR | |
| SEQ ID NO: 87 | m208 | Ala$^{117}$---$^{118}$---$^{119}$Trp$^{120}$Arg$^{121}$ is: AXXWR | |
| SEQ ID NO: 88 | m203 | Arg$^{117}$---$^{118}$---$^{119}$Trp$^{120}$Ser$^{121}$ is: RXXWS | |
| SEQ ID NO: 89 | m209 | Asn$^{117}$---$^{118}$---$^{119}$Trp$^{120}$Arg$^{121}$ is: NXXWR | |
| SEQ ID NO: 90 | m200 | Lys$^{117}$---$^{118}$---$^{119}$Trp$^{120}$Ser$^{121}$ is: KXXWS | |
| SEQ ID NO: 91 | m201 | Ser$^{117}$---$^{118}$---$^{119}$Val$^{120}$Phe$^{121}$ is: SXXVF | |
| SEQ ID NO: 92 | m211 | Lys$^{117}$---$^{118}$---$^{119}$Trp$^{120}$Thr$^{121}$ is: KXXWT | |
| SEQ ID NO: 93 | m300 | Ala$^{117}$---$^{118}$---$^{119}$Trp$^{120}$Tyr$^{21}$ is: AXXWY | |
| SEQ ID NO: 94 | m301 | His$^{117}$---$^{118}$---$^{119}$Trp$^{120}$Met$^{121}$ is: HXXWM | |
| SEQ ID NO: 95 | m302 | His$^{117}$---$^{118}$---$^{119}$Trp$^{120}$Tyr$^{121}$ is: HXXWY | |

| SEQ ID NO: 96 | m303 | Glu$^{117}$---$^{118}$---$^{119}$Trp$^{120}$Tyr$^{121}$<br>is: EXXWY |
| --- | --- | --- |
| SEQ ID NO: 97 | m304 | Gln$^{117}$---$^{118}$---$^{119}$Trp$^{120}$Tyr$^{121}$<br>is: QXXWY |
| SEQ ID NO: 98 | motif1<br>(FIG. 2)<br>motif2<br>consensus<br>sequence2 | Xaa Asn Ala Gly Zaa,<br>Xaa is Glu, Asp, Arg, His, Asn, Gln, Thr, Ser, Leu, Met<br>and Zaa is Phe, Tyr, Met is XNAGX<br>Aaa$^{117}$Baa$^{120}$Caa$^{121}$<br>wherein Aaa may be Tyr, Phe, Arg, Trp or Gln, Baa may<br>be Tyr, Phe, Leu, Ile or Met and Caa may be any amino<br>acid, wherein Caa121 is preferably a Leu, an Ile, a Met,<br>a Gly, a Gly, a Trp, a Ser, an Ala or a Val residue |
| SEQ ID NO: 99 | Motif2<br>(FIG. 2) | Xaa-Asn-Ala-Yaa-Zaa,<br>wherein Xaa is Tyr, Phe, Arg, Trp, Gln;<br>Yaa is Tyr, Phe, Leu, Ile, Met and<br>Zaa is Leu, Ile, Met, Gln, Gly, Trp, Ser, Ala, Val<br>Is XNAXX |
| SEQ ID NO: 100 | motif3<br>consensus<br>sequence3 | Daa$^{117}$Eaa$^{118}$Faa$^{119}$Gaa$^{120}$Haa$^{121}$, wherein Daa and Haa<br>may be any amino acid and Eaa and Faa are both<br>deleted and Gaa may be Trp or Val,<br>wherein Daa$^{117}$ is preferably a His, a Glu, a Gln, a Thr,<br>an Ala or an Ile residue and wherein Haa$^{121}$ is<br>preferably a Tyr, a Leu, a Met, or an Arg residue<br>is XXXXX |

What is claimed is:

1. A streptavidin mutein, comprising: the amino acid sequence of the mutein m1-9C (SEQ ID NO: 16).

2. The streptavidin mutein according to claim 1, wherein the mutein is a mutein of a minimal streptavidin which begins N-terminally in the region of the amino acids 10 to 16 of SEQ ID NO: 1 and terminates C-terminally in the region of the amino acids 133-142 of SEQ ID NO: 1.

3. The streptavidin mutein according to claim 1, wherein the streptavidin mutein consists of the sequence of the mutein m1-9C (SEQ ID NO: 16).

4. A solid phase having immobilized thereon the streptavidin mutein of claim 1.

5. A nucleic acid molecule, comprising a sequence coding for the streptavidin mutein as defined in claim 1.

6. A method of isolating, purifying or determining under denaturing conditions a protein that is fused with a) a peptide sequence of the formula Trp-Xaa-His-Pro-Gln-Phe-Yaa-Zaa (SEQ ID NO: 8) in which Xaa represents an arbitrary amino acid and Yaa and Zaa either both denote Gly or Yaa denotes Glu and Zaa denotes Arg or Lys, or b) a peptide sequence that comprises a sequential arrangement of at least two streptavidin-binding modules, wherein the distance between the two modules is at least 0 and not greater than 50 amino acids, wherein one binding module has 3 to 8 amino acids and comprises at least the sequence -His-Pro-Baa-, where Baa is glutamine, asparagine or methionine, and wherein the other binding module has the sequence -Oaa-Xaa-His-Pro-Gln-Phe-Yaa-Zaa- (SEQ ID NO: 9) where Oaa is Trp, Lys or Arg, Xaa is any amino acid and where either Yaa and Zaa are both Gly or Yaa is Glu and Zaa is Lys or Arg, the method comprising contacting a sample containing the protein with the streptavidin mutein of claim 1, under suitable conditions to bind the peptide sequence to the streptavidin mutein, and separating the resulting complex from said sample.

* * * * *

SEQUENCE LISTING

<160> NUMBER OF SEQ ID NOS: 100

<210> SEQ ID NO 1
<211> LENGTH: 159
<212> TYPE: PRT
<213> ORGANISM: artificial sequence
<220> FEATURE:
<223> OTHER INFORMATION: mature wild-type streptavidin (residues 1 to
      159)

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

```
<210> SEQ ID NO 2
<211> LENGTH: 126
<212> TYPE: PRT
<213> ORGANISM: artificial sequence
<220> FEATURE:
<223> OTHER INFORMATION: mature wild-type streptavidin (residues 14 to
      139)

<400> SEQUENCE: 2

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 3
<211> LENGTH: 8
<212> TYPE: PRT
<213> ORGANISM: artificial sequence
<220> FEATURE:
<223> OTHER INFORMATION: Step-tag II affinity tag

<400> SEQUENCE: 3

Trp Ser His Pro Gln Phe Glu Lys
1               5

<210> SEQ ID NO 4
<211> LENGTH: 8
<212> TYPE: PRT
<213> ORGANISM: artificial sequence
<220> FEATURE:
<223> OTHER INFORMATION: Strep-tag affinity tag

<400> SEQUENCE: 4

Trp Arg His Pro Gln Phe Gly Gly
1               5

<210> SEQ ID NO 5
<211> LENGTH: 28
<212> TYPE: PRT
<213> ORGANISM: artificial sequence
<220> FEATURE:
<223> OTHER INFORMATION: di-tag3 sequence

<400> SEQUENCE: 5

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 6
<211> LENGTH: 24
```

```
<212> TYPE: PRT
<213> ORGANISM: artificial sequence
<220> FEATURE:
<223> OTHER INFORMATION: di-tag2 sequence

<400> SEQUENCE: 6

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 7
<211> LENGTH: 28
<212> TYPE: PRT
<213> ORGANISM: artificial sequence
<220> FEATURE:
<223> OTHER INFORMATION: Twin-Strep-tag

<400> SEQUENCE: 7

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 8
<211> LENGTH: 8
<212> TYPE: PRT
<213> ORGANISM: artificial sequence
<220> FEATURE:
<223> OTHER INFORMATION: peptide sequence
<220> FEATURE:
<221> NAME/KEY: MISC_FEATURE
<222> LOCATION: (2)..(2)
<223> OTHER INFORMATION: arbitrary amino acid
<220> FEATURE:
<221> NAME/KEY: MISC_FEATURE
<222> LOCATION: (7)..(8)
<223> OTHER INFORMATION: position 7 and 8 G or position 7 E and position
     8 R or K

<400> SEQUENCE: 8

Trp Xaa His Pro Gln Phe Xaa Xaa
1               5

<210> SEQ ID NO 9
<211> LENGTH: 8
<212> TYPE: PRT
<213> ORGANISM: artificial sequence
<220> FEATURE:
<223> OTHER INFORMATION: binding molecule
<220> FEATURE:
<221> NAME/KEY: MISC_FEATURE
<222> LOCATION: (1)..(1)
<223> OTHER INFORMATION: position 1 is W, K or R
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (7)..(8)
<223> OTHER INFORMATION: positions 7 and 8 both G or position 7 E and
     position 8 K or R

<400> SEQUENCE: 9

Xaa Xaa His Pro Gln Phe Xaa Xaa
1               5

<210> SEQ ID NO 10
```

```
<211> LENGTH: 4
<212> TYPE: PRT
<213> ORGANISM: artificial sequence
<220> FEATURE:
<223> OTHER INFORMATION: amino acid position 44 to 47 of wild type
      streptavidin

<400> SEQUENCE: 10

Val Thr Ala Arg
1

<210> SEQ ID NO 11
<211> LENGTH: 4
<212> TYPE: PRT
<213> ORGANISM: artificial sequence
<220> FEATURE:
<223> OTHER INFORMATION: mutein of wildtype streptavidin at amino acid
      positions 44 to 47

<400> SEQUENCE: 11

Ile Gly Ala Arg
1

<210> SEQ ID NO 12
<211> LENGTH: 126
<212> TYPE: PRT
<213> ORGANISM: artificial sequence
<220> FEATURE:
<223> OTHER INFORMATION: mutein "1"

<400> SEQUENCE: 12

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 13
<211> LENGTH: 124
<212> TYPE: PRT
<213> ORGANISM: artificial sequence
<220> FEATURE:
<223> OTHER INFORMATION: mutein m302

<400> SEQUENCE: 13

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45
```

```
Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu His Trp Tyr Ser Thr Leu Val Gly His
            100                 105                 110

Asp Thr Phe Thr Lys Val Lys Pro Ser Ala Ala Ser
            115                 120
```

<210> SEQ ID NO 14
<211> LENGTH: 124
<212> TYPE: PRT
<213> ORGANISM: artificial sequence
<220> FEATURE:
<223> OTHER INFORMATION: mutein m302C

<400> SEQUENCE: 14

```
Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Tyr Val Thr
                 20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu His Trp Tyr Ser Thr Leu Val Gly Cys
            100                 105                 110

Asp Thr Phe Thr Lys Val Lys Pro Ser Ala Ala Ser
            115                 120
```

<210> SEQ ID NO 15
<211> LENGTH: 126
<212> TYPE: PRT
<213> ORGANISM: artificial sequence
<220> FEATURE:
<223> OTHER INFORMATION: mutein m1-9

<400> SEQUENCE: 15

```
Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Tyr Val Thr
                 20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Glu Asn Ala Gly Tyr Ser Thr Leu Val
            100                 105                 110
```

```
Gly His Asp Thr Phe Thr Lys Val Lys Pro Ser Ala Ala Ser
        115                 120                 125
```

<210> SEQ ID NO 16
<211> LENGTH: 126
<212> TYPE: PRT
<213> ORGANISM: artificial sequence
<220> FEATURE:
<223> OTHER INFORMATION: mutein m1-9C

<400> SEQUENCE: 16

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Gly Tyr Ser Thr Leu Val
            100                 105                 110

Gly Cys Asp Thr Phe Thr Lys Val Lys Pro Ser Ala Ala Ser
        115                 120                 125
```

<210> SEQ ID NO 17
<211> LENGTH: 8
<212> TYPE: PRT
<213> ORGANISM: artificial sequence
<220> FEATURE:
<223> OTHER INFORMATION: sequence positions 114 to 121 of streptavidin

<400> SEQUENCE: 17

```
Thr Thr Glu Ala Asn Ala Trp Lys
1               5
```

<210> SEQ ID NO 18
<211> LENGTH: 14
<212> TYPE: PRT
<213> ORGANISM: artificial sequence
<220> FEATURE:
<223> OTHER INFORMATION: amino acid positions 114 to 121 of streptavidin
      replaced by this sequence according to Fletcher et al.

<400> SEQUENCE: 18

```
His Pro Tyr Phe Tyr Ala Pro Glu Leu Leu Phe Phe Ala Lys
1               5                   10
```

<210> SEQ ID NO 19
<211> LENGTH: 16
<212> TYPE: PRT
<213> ORGANISM: artificial sequence
<220> FEATURE:
<223> OTHER INFORMATION: amino acid positions 114 to 121 of streptavidin
      replaced by this sequence according to Fletcher et al.

<400> SEQUENCE: 19

```
Glu Gly Gly Lys Glu Thr Leu Thr Pro Ser Glu Leu Arg Asp Leu Val
1               5                   10                  15
```

```
<210> SEQ ID NO 20
<211> LENGTH: 5
<212> TYPE: PRT
<213> ORGANISM: artificial sequence
<220> FEATURE:
<223> OTHER INFORMATION: wild type streptavidin (positions 117 to 121)

<400> SEQUENCE: 20

Ala Asn Ala Trp Lys
1               5

<210> SEQ ID NO 21
<211> LENGTH: 5
<212> TYPE: PRT
<213> ORGANISM: Artificial Sequence
<220> FEATURE:
<223> OTHER INFORMATION: m36 fragment

<400> SEQUENCE: 21

Tyr Asn Ala Phe Met
1               5

<210> SEQ ID NO 22
<211> LENGTH: 5
<212> TYPE: PRT
<213> ORGANISM: Artificial Sequence
<220> FEATURE:
<223> OTHER INFORMATION: m23 fragment

<400> SEQUENCE: 22

Tyr Asn Ala Tyr Ala
1               5

<210> SEQ ID NO 23
<211> LENGTH: 5
<212> TYPE: PRT
<213> ORGANISM: Artificial Sequence
<220> FEATURE:
<223> OTHER INFORMATION: m41 fragment
<220> FEATURE:
<221> NAME/KEY: MISC_FEATURE
<222> LOCATION: (2)..(3)
<223> OTHER INFORMATION: amino acid deletion

<400> SEQUENCE: 23

Ala Xaa Xaa Trp Tyr
1               5

<210> SEQ ID NO 24
<211> LENGTH: 5
<212> TYPE: PRT
<213> ORGANISM: Artificial Sequence
<220> FEATURE:
<223> OTHER INFORMATION: m4 fragment

<400> SEQUENCE: 24

Asp Asn Ala Gly Phe
1               5

<210> SEQ ID NO 25
<211> LENGTH: 5
<212> TYPE: PRT
<213> ORGANISM: Artificial Sequence
<220> FEATURE:
<223> OTHER INFORMATION: m12 fragment

<400> SEQUENCE: 25
```

Arg Asn Ala Gly Phe
1               5

<210> SEQ ID NO 26
<211> LENGTH: 5
<212> TYPE: PRT
<213> ORGANISM: Artificial Sequence
<220> FEATURE:
<223> OTHER INFORMATION: m22 fragment

<400> SEQUENCE: 26

Gln Asn Ala Gly Phe
1               5

<210> SEQ ID NO 27
<211> LENGTH: 5
<212> TYPE: PRT
<213> ORGANISM: Artificial Sequence
<220> FEATURE:
<223> OTHER INFORMATION: m31 fragment

<400> SEQUENCE: 27

Phe Asn Ala Ser Trp
1               5

<210> SEQ ID NO 28
<211> LENGTH: 5
<212> TYPE: PRT
<213> ORGANISM: Artificial Sequence
<220> FEATURE:
<223> OTHER INFORMATION: m32 fragment

<400> SEQUENCE: 28

Asp Asn Ala Val Met
1               5

<210> SEQ ID NO 29
<211> LENGTH: 5
<212> TYPE: PRT
<213> ORGANISM: Artificial Sequence
<220> FEATURE:
<223> OTHER INFORMATION: m35 fragment
<220> FEATURE:
<221> NAME/KEY: MISC_FEATURE
<222> LOCATION: (2)..(3)
<223> OTHER INFORMATION: amino acid deletion

<400> SEQUENCE: 29

Ala Xaa Xaa Trp Met
1               5

<210> SEQ ID NO 30
<211> LENGTH: 5
<212> TYPE: PRT
<213> ORGANISM: Artificial Sequence
<220> FEATURE:
<223> OTHER INFORMATION: m38 fragment

<400> SEQUENCE: 30

Glu Asn Ala Gly Phe
1               5

<210> SEQ ID NO 31
<211> LENGTH: 5
<212> TYPE: PRT
<213> ORGANISM: Artificial Sequence
<220> FEATURE:
<223> OTHER INFORMATION: m40 fragment

```
<400> SEQUENCE: 31

Tyr Asn Ala Tyr Ser
1               5

<210> SEQ ID NO 32
<211> LENGTH: 5
<212> TYPE: PRT
<213> ORGANISM: Artificial Sequence
<220> FEATURE:
<223> OTHER INFORMATION: m 42 fragment

<400> SEQUENCE: 32

Phe Asn Ala Tyr Gly
1               5

<210> SEQ ID NO 33
<211> LENGTH: 5
<212> TYPE: PRT
<213> ORGANISM: Artificial Sequence
<220> FEATURE:
<223> OTHER INFORMATION: m45 fragment

<400> SEQUENCE: 33

Tyr Asn Ala Gly Phe
1               5

<210> SEQ ID NO 34
<211> LENGTH: 5
<212> TYPE: PRT
<213> ORGANISM: Artificial Sequence
<220> FEATURE:
<223> OTHER INFORMATION: m46 fragment

<400> SEQUENCE: 34

Arg Asn Ala Tyr Ala
1               5

<210> SEQ ID NO 35
<211> LENGTH: 5
<212> TYPE: PRT
<213> ORGANISM: Artificial Sequence
<220> FEATURE:
<223> OTHER INFORMATION: m47 fragment

<400> SEQUENCE: 35

Trp Asn Ala Tyr Gly
1               5

<210> SEQ ID NO 36
<211> LENGTH: 5
<212> TYPE: PRT
<213> ORGANISM: Artificial Sequence
<220> FEATURE:
<223> OTHER INFORMATION: m7 fragment

<400> SEQUENCE: 36

Leu Asn Ala Gly Phe
1               5

<210> SEQ ID NO 37
<211> LENGTH: 5
<212> TYPE: PRT
<213> ORGANISM: Artificial Sequence
<220> FEATURE:
<223> OTHER INFORMATION: m10 fragment
```

```
<400> SEQUENCE: 37

His Asn Ala Gly Tyr
1               5

<210> SEQ ID NO 38
<211> LENGTH: 5
<212> TYPE: PRT
<213> ORGANISM: Artificial Sequence
<220> FEATURE:
<223> OTHER INFORMATION: m17 fragment

<400> SEQUENCE: 38

Met Asn Ala Gly Phe
1               5

<210> SEQ ID NO 39
<211> LENGTH: 5
<212> TYPE: PRT
<213> ORGANISM: Artificial Sequence
<220> FEATURE:
<223> OTHER INFORMATION: m21 fragment

<400> SEQUENCE: 39

Arg Asn Ala Gly Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: m24 fragment

<400> SEQUENCE: 40

Glu Asn Ala Gly Trp
1               5

<210> SEQ ID NO 41
<211> LENGTH: 5
<212> TYPE: PRT
<213> ORGANISM: Artificial Sequence
<220> FEATURE:
<223> OTHER INFORMATION: m27 fragment

<400> SEQUENCE: 41

His Asn Ala Gly Phe
1               5

<210> SEQ ID NO 42
<211> LENGTH: 5
<212> TYPE: PRT
<213> ORGANISM: Artificial Sequence
<220> FEATURE:
<223> OTHER INFORMATION: m28 fragment

<400> SEQUENCE: 42

Ser Asn Ala Gly Phe
1               5

<210> SEQ ID NO 43
<211> LENGTH: 5
<212> TYPE: PRT
<213> ORGANISM: Artificial Sequence
<220> FEATURE:
<223> OTHER INFORMATION: m30 fragment

<400> SEQUENCE: 43
```

Thr Asn Ala Gly Phe
1               5

<210> SEQ ID NO 44
<211> LENGTH: 5
<212> TYPE: PRT
<213> ORGANISM: Artificial Sequence
<220> FEATURE:
<223> OTHER INFORMATION: m33 fragment

<400> SEQUENCE: 44

Asn Asn Ala Gly Phe
1               5

<210> SEQ ID NO 45
<211> LENGTH: 5
<212> TYPE: PRT
<213> ORGANISM: Artificial Sequence
<220> FEATURE:
<223> OTHER INFORMATION: m1 frag,ent

<400> SEQUENCE: 45

Glu Asn Ala Gly Met
1               5

<210> SEQ ID NO 46
<211> LENGTH: 5
<212> TYPE: PRT
<213> ORGANISM: Artificial Sequence
<220> FEATURE:
<223> OTHER INFORMATION: m3 fragment

<400> SEQUENCE: 46

Trp Asn Ala Cys Cys
1               5

<210> SEQ ID NO 47
<211> LENGTH: 5
<212> TYPE: PRT
<213> ORGANISM: Artificial Sequence
<220> FEATURE:
<223> OTHER INFORMATION: m8 fragment

<400> SEQUENCE: 47

Met Asn Ala Phe Val
1               5

<210> SEQ ID NO 48
<211> LENGTH: 5
<212> TYPE: PRT
<213> ORGANISM: Artificial Sequence
<220> FEATURE:
<223> OTHER INFORMATION: m15 fragment

<400> SEQUENCE: 48

Ala Asn Ala Asp Trp
1               5

<210> SEQ ID NO 49
<211> LENGTH: 5
<212> TYPE: PRT
<213> ORGANISM: Artificial Sequence
<220> FEATURE:
<223> OTHER INFORMATION: m6 fragment

<400> SEQUENCE: 49

Ser Asn Ala Met Met
1               5

<210> SEQ ID NO 50
<211> LENGTH: 5
<212> TYPE: PRT
<213> ORGANISM: Artificial Sequence
<220> FEATURE:
<223> OTHER INFORMATION: m9 fragment

<400> SEQUENCE: 50

Arg Asn Ala Val Val
1               5

<210> SEQ ID NO 51
<211> LENGTH: 5
<212> TYPE: PRT
<213> ORGANISM: Artificial Sequence
<220> FEATURE:
<223> OTHER INFORMATION: m20 fragment

<400> SEQUENCE: 51

Ser Asn Ala Ser Phe
1               5

<210> SEQ ID NO 52
<211> LENGTH: 5
<212> TYPE: PRT
<213> ORGANISM: Artificial Sequence
<220> FEATURE:
<223> OTHER INFORMATION: m34 fragment
<220> FEATURE:
<221> NAME/KEY: MISC_FEATURE
<222> LOCATION: (2)..(3)
<223> OTHER INFORMATION: amino acid deletion

<400> SEQUENCE: 52

Ala Xaa Xaa Trp Asp
1               5

<210> SEQ ID NO 53
<211> LENGTH: 5
<212> TYPE: PRT
<213> ORGANISM: Artificial Sequence
<220> FEATURE:
<223> OTHER INFORMATION: m14 fragment

<400> SEQUENCE: 53

Arg Asn Ala Arg Ala
1               5

<210> SEQ ID NO 54
<211> LENGTH: 5
<212> TYPE: PRT
<213> ORGANISM: Artificial Sequence
<220> FEATURE:
<223> OTHER INFORMATION: m18 fragment

<400> SEQUENCE: 54

Ser Asn Ala Ala Phe
1               5

<210> SEQ ID NO 55
<211> LENGTH: 5
<212> TYPE: PRT
<213> ORGANISM: Artificial Sequence
<220> FEATURE:
<223> OTHER INFORMATION: m19 fragment

<400> SEQUENCE: 55

Gly Asn Ala Met Met
1               5

<210> SEQ ID NO 56
<211> LENGTH: 5
<212> TYPE: PRT
<213> ORGANISM: Artificial Sequence
<220> FEATURE:
<223> OTHER INFORMATION: m8 fragment

<400> SEQUENCE: 56

Glu Asn Ala Gly Phe
1               5

<210> SEQ ID NO 57
<211> LENGTH: 5
<212> TYPE: PRT
<213> ORGANISM: Artificial Sequence
<220> FEATURE:
<223> OTHER INFORMATION: m21 fragment

<400> SEQUENCE: 57

Asp Asn Ala Gly Tyr
1               5

<210> SEQ ID NO 58
<211> LENGTH: 5
<212> TYPE: PRT
<213> ORGANISM: Artificial Sequence
<220> FEATURE:
<223> OTHER INFORMATION: m9 fragment

<400> SEQUENCE: 58

Glu Asn Ala Gly Tyr
1               5

<210> SEQ ID NO 59
<211> LENGTH: 5
<212> TYPE: PRT
<213> ORGANISM: Artificial Sequence
<220> FEATURE:
<223> OTHER INFORMATION: m1 fragment

<400> SEQUENCE: 59

Arg Asn Ala Met Met
1               5

<210> SEQ ID NO 60
<211> LENGTH: 5
<212> TYPE: PRT
<213> ORGANISM: Artificial Sequence
<220> FEATURE:
<223> OTHER INFORMATION: m2 fragment

<400> SEQUENCE: 60

Arg Asn Ala Gly Phe
1               5

<210> SEQ ID NO 61
<211> LENGTH: 5
<212> TYPE: PRT
<213> ORGANISM: Artificial Sequence
<220> FEATURE:
<223> OTHER INFORMATION: m3 fragment

```
<400> SEQUENCE: 61

Ala Asn Ala Pro Ala
1               5

<210> SEQ ID NO 62
<211> LENGTH: 5
<212> TYPE: PRT
<213> ORGANISM: Artificial Sequence
<220> FEATURE:
<223> OTHER INFORMATION: m5 fragment

<400> SEQUENCE: 62

Ala Asn Ala Met Val
1               5

<210> SEQ ID NO 63
<211> LENGTH: 5
<212> TYPE: PRT
<213> ORGANISM: Artificial Sequence
<220> FEATURE:
<223> OTHER INFORMATION: m13 fragment

<400> SEQUENCE: 63

Gln Asn Ala Ser Ala
1               5

<210> SEQ ID NO 64
<211> LENGTH: 5
<212> TYPE: PRT
<213> ORGANISM: Artificial Sequence
<220> FEATURE:
<223> OTHER INFORMATION: m14 fragment

<400> SEQUENCE: 64

Ala Asn Ala Gly Phe
1               5

<210> SEQ ID NO 65
<211> LENGTH: 5
<212> TYPE: PRT
<213> ORGANISM: Artificial Sequence
<220> FEATURE:
<223> OTHER INFORMATION: m24 fragemnt

<400> SEQUENCE: 65

Gln Asn Ala Met Val
1               5

<210> SEQ ID NO 66
<211> LENGTH: 5
<212> TYPE: PRT
<213> ORGANISM: Artificial Sequence
<220> FEATURE:
<223> OTHER INFORMATION: m4 fragment

<400> SEQUENCE: 66

Asn Asn Ala Gly Tyr
1               5

<210> SEQ ID NO 67
<211> LENGTH: 5
<212> TYPE: PRT
<213> ORGANISM: Artificial Sequence
<220> FEATURE:
<223> OTHER INFORMATION: m6 fragment

<400> SEQUENCE: 67
```

```
Ala Asn Ala Ala Val
1               5

<210> SEQ ID NO 68
<211> LENGTH: 5
<212> TYPE: PRT
<213> ORGANISM: Artificial Sequence
<220> FEATURE:
<223> OTHER INFORMATION: m7 fragment

<400> SEQUENCE: 68

Ser Asn Ala Met Ile
1               5

<210> SEQ ID NO 69
<211> LENGTH: 5
<212> TYPE: PRT
<213> ORGANISM: Artificial Sequence
<220> FEATURE:
<223> OTHER INFORMATION: m10 fragment

<400> SEQUENCE: 69

His Asn Ala Gly Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: m15 fragment

<400> SEQUENCE: 70

Ser Asn Ala Met Ala
1               5

<210> SEQ ID NO 71
<211> LENGTH: 5
<212> TYPE: PRT
<213> ORGANISM: Artificial Sequence
<220> FEATURE:
<223> OTHER INFORMATION: m23 fragment

<400> SEQUENCE: 71

Gln Asn Ala Val Ala
1               5

<210> SEQ ID NO 72
<211> LENGTH: 5
<212> TYPE: PRT
<213> ORGANISM: Artificial Sequence
<220> FEATURE:
<223> OTHER INFORMATION: m17 fragment

<400> SEQUENCE: 72

Tyr Asn Ala Tyr Met
1               5

<210> SEQ ID NO 73
<211> LENGTH: 5
<212> TYPE: PRT
<213> ORGANISM: Artificial Sequence
<220> FEATURE:
<223> OTHER INFORMATION: m12 fragment

<400> SEQUENCE: 73
```

```
Leu Asn Ala Trp Gly
1               5

<210> SEQ ID NO 74
<211> LENGTH: 5
<212> TYPE: PRT
<213> ORGANISM: Artificial Sequence
<220> FEATURE:
<223> OTHER INFORMATION: m20 fragment

<400> SEQUENCE: 74

His Asn Ala Ser Met
1               5

<210> SEQ ID NO 75
<211> LENGTH: 5
<212> TYPE: PRT
<213> ORGANISM: Artificial Sequence
<220> FEATURE:
<223> OTHER INFORMATION: m101 fragment

<400> SEQUENCE: 75

Tyr Asn Ala Phe Leu
1               5

<210> SEQ ID NO 76
<211> LENGTH: 5
<212> TYPE: PRT
<213> ORGANISM: Artificial Sequence
<220> FEATURE:
<223> OTHER INFORMATION: m106 fragment

<400> SEQUENCE: 76

Phe Asn Ala Phe Leu
1               5

<210> SEQ ID NO 77
<211> LENGTH: 5
<212> TYPE: PRT
<213> ORGANISM: Artificial Sequence
<220> FEATURE:
<223> OTHER INFORMATION: m111 fragment

<400> SEQUENCE: 77

Tyr Asn Ala Leu Trp
1               5

<210> SEQ ID NO 78
<211> LENGTH: 5
<212> TYPE: PRT
<213> ORGANISM: Artificial Sequence
<220> FEATURE:
<223> OTHER INFORMATION: m100 fragment

<400> SEQUENCE: 78

Phe Asn Ala Tyr Ile
1               5

<210> SEQ ID NO 79
<211> LENGTH: 5
<212> TYPE: PRT
<213> ORGANISM: Artificial Sequence
<220> FEATURE:
<223> OTHER INFORMATION: m110 fragment

<400> SEQUENCE: 79

Tyr Asn Ala Tyr Leu
```

```
<210> SEQ ID NO 80
<211> LENGTH: 5
<212> TYPE: PRT
<213> ORGANISM: Artificial Sequence
<220> FEATURE:
<223> OTHER INFORMATION: m104 fragment

<400> SEQUENCE: 80

Tyr Asn Ala Tyr Gln
1               5

<210> SEQ ID NO 81
<211> LENGTH: 5
<212> TYPE: PRT
<213> ORGANISM: Artificial Sequence
<220> FEATURE:
<223> OTHER INFORMATION: m108 fragment

<400> SEQUENCE: 81

Phe Asn Ala Ile Trp
1               5

<210> SEQ ID NO 82
<211> LENGTH: 5
<212> TYPE: PRT
<213> ORGANISM: Artificial Sequence
<220> FEATURE:
<223> OTHER INFORMATION: m207 fragment
<220> FEATURE:
<221> NAME/KEY: MISC_FEATURE
<222> LOCATION: (2)..(3)
<223> OTHER INFORMATION: amino acid deletion

<400> SEQUENCE: 82

Thr Xaa Xaa Trp Leu
1               5

<210> SEQ ID NO 83
<211> LENGTH: 5
<212> TYPE: PRT
<213> ORGANISM: Artificial Sequence
<220> FEATURE:
<223> OTHER INFORMATION: m212 fragment
<220> FEATURE:
<221> NAME/KEY: MISC_FEATURE
<222> LOCATION: (2)..(3)
<223> OTHER INFORMATION: amino acid deletion

<400> SEQUENCE: 83

His Xaa Xaa Trp Leu
1               5

<210> SEQ ID NO 84
<211> LENGTH: 5
<212> TYPE: PRT
<213> ORGANISM: Artificial Sequence
<220> FEATURE:
<223> OTHER INFORMATION: m202 fragment
<220> FEATURE:
<221> NAME/KEY: MISC_FEATURE
<222> LOCATION: (2)..(3)
<223> OTHER INFORMATION: amino acid deletion

<400> SEQUENCE: 84

Ile Xaa Xaa Trp Arg
1               5
```

```
<210> SEQ ID NO 85
<211> LENGTH: 5
<212> TYPE: PRT
<213> ORGANISM: Artificial Sequence
<220> FEATURE:
<223> OTHER INFORMATION: m204 fragment
<220> FEATURE:
<221> NAME/KEY: MISC_FEATURE
<222> LOCATION: (2)..(3)
<223> OTHER INFORMATION: amino acid deletion

<400> SEQUENCE: 85

His Xaa Xaa Trp Thr
1               5

<210> SEQ ID NO 86
<211> LENGTH: 5
<212> TYPE: PRT
<213> ORGANISM: Artificial Sequence
<220> FEATURE:
<223> OTHER INFORMATION: m206 fragment
<220> FEATURE:
<221> NAME/KEY: MISC_FEATURE
<222> LOCATION: (2)..(3)
<223> OTHER INFORMATION: amino acid deletion

<400> SEQUENCE: 86

Thr Xaa Xaa Trp Arg
1               5

<210> SEQ ID NO 87
<211> LENGTH: 5
<212> TYPE: PRT
<213> ORGANISM: Artificial Sequence
<220> FEATURE:
<223> OTHER INFORMATION: m208 fragment
<220> FEATURE:
<221> NAME/KEY: MISC_FEATURE
<222> LOCATION: (2)..(3)
<223> OTHER INFORMATION: amino acid deletion

<400> SEQUENCE: 87

Ala Xaa Xaa Trp Arg
1               5

<210> SEQ ID NO 88
<211> LENGTH: 5
<212> TYPE: PRT
<213> ORGANISM: Artificial Sequence
<220> FEATURE:
<223> OTHER INFORMATION: m203 fragment
<220> FEATURE:
<221> NAME/KEY: MISC_FEATURE
<222> LOCATION: (2)..(3)
<223> OTHER INFORMATION: amino acid deletion

<400> SEQUENCE: 88

Arg Xaa Xaa Trp Ser
1               5

<210> SEQ ID NO 89
<211> LENGTH: 5
<212> TYPE: PRT
<213> ORGANISM: Artificial Sequence
<220> FEATURE:
<223> OTHER INFORMATION: m209 fragment
<220> FEATURE:
<221> NAME/KEY: MISC_FEATURE
<222> LOCATION: (2)..(3)
<223> OTHER INFORMATION: amino acid deletion
```

<400> SEQUENCE: 89

Asn Xaa Xaa Trp Arg
1               5

<210> SEQ ID NO 90
<211> LENGTH: 5
<212> TYPE: PRT
<213> ORGANISM: Artificial Sequence
<220> FEATURE:
<223> OTHER INFORMATION: m200 fragment
<220> FEATURE:
<221> NAME/KEY: MISC_FEATURE
<222> LOCATION: (2)..(3)
<223> OTHER INFORMATION: amino acid deletion

<400> SEQUENCE: 90

Lys Xaa Xaa Trp Ser
1               5

<210> SEQ ID NO 91
<211> LENGTH: 5
<212> TYPE: PRT
<213> ORGANISM: Artificial Sequence
<220> FEATURE:
<223> OTHER INFORMATION: m201 fragment
<220> FEATURE:
<221> NAME/KEY: MISC_FEATURE
<222> LOCATION: (2)..(3)
<223> OTHER INFORMATION: amino acid deletion

<400> SEQUENCE: 91

Ser Xaa Xaa Val Phe
1               5

<210> SEQ ID NO 92
<211> LENGTH: 5
<212> TYPE: PRT
<213> ORGANISM: Artificial Sequence
<220> FEATURE:
<223> OTHER INFORMATION: m211 fragment
<220> FEATURE:
<221> NAME/KEY: MISC_FEATURE
<222> LOCATION: (2)..(3)
<223> OTHER INFORMATION: amino acid deletion

<400> SEQUENCE: 92

Lys Xaa Xaa Trp Thr
1               5

<210> SEQ ID NO 93
<211> LENGTH: 5
<212> TYPE: PRT
<213> ORGANISM: Artificial Sequence
<220> FEATURE:
<223> OTHER INFORMATION: m300 fragment
<220> FEATURE:
<221> NAME/KEY: MISC_FEATURE
<222> LOCATION: (2)..(3)
<223> OTHER INFORMATION: amino acid deletion

<400> SEQUENCE: 93

Ala Xaa Xaa Trp Tyr
1               5

<210> SEQ ID NO 94
<211> LENGTH: 5
<212> TYPE: PRT
<213> ORGANISM: Artificial Sequence

```
<220> FEATURE:
<223> OTHER INFORMATION: m301 fragment
<220> FEATURE:
<221> NAME/KEY: MISC_FEATURE
<222> LOCATION: (2)..(3)
<223> OTHER INFORMATION: amino acid deletion

<400> SEQUENCE: 94

His Xaa Xaa Trp Met
1               5

<210> SEQ ID NO 95
<211> LENGTH: 5
<212> TYPE: PRT
<213> ORGANISM: Artificial Sequence
<220> FEATURE:
<223> OTHER INFORMATION: m302 fragment
<220> FEATURE:
<221> NAME/KEY: MISC_FEATURE
<222> LOCATION: (2)..(3)
<223> OTHER INFORMATION: amino acid deletion

<400> SEQUENCE: 95

His Xaa Xaa Trp Tyr
1               5

<210> SEQ ID NO 96
<211> LENGTH: 5
<212> TYPE: PRT
<213> ORGANISM: Artificial Sequence
<220> FEATURE:
<223> OTHER INFORMATION: m303 fragment
<220> FEATURE:
<221> NAME/KEY: MISC_FEATURE
<222> LOCATION: (2)..(3)
<223> OTHER INFORMATION: amino acid deletion

<400> SEQUENCE: 96

Glu Xaa Xaa Trp Tyr
1               5

<210> SEQ ID NO 97
<211> LENGTH: 5
<212> TYPE: PRT
<213> ORGANISM: Artificial Sequence
<220> FEATURE:
<223> OTHER INFORMATION: m304 fragment
<220> FEATURE:
<221> NAME/KEY: MISC_FEATURE
<222> LOCATION: (2)..(3)
<223> OTHER INFORMATION: amino acid deletion

<400> SEQUENCE: 97

Gln Xaa Xaa Trp Tyr
1               5

<210> SEQ ID NO 98
<211> LENGTH: 5
<212> TYPE: PRT
<213> ORGANISM: artificial sequence
<220> FEATURE:
<223> OTHER INFORMATION: motif 1 (figure 2)
<220> FEATURE:
<221> NAME/KEY: MISC_FEATURE
<222> LOCATION: (1)..(1)
<223> OTHER INFORMATION: position 1 is E,D, R, H, N, Q, T, S, L or M
<220> FEATURE:
<221> NAME/KEY: MISC_FEATURE
<222> LOCATION: (5)..(5)
<223> OTHER INFORMATION: position 5 is F, Y or M
```

```
<400> SEQUENCE: 98

Xaa Asn Ala Gly Xaa
 1               5

<210> SEQ ID NO 99
<211> LENGTH: 5
<212> TYPE: PRT
<213> ORGANISM: artificial sequence
<220> FEATURE:
<223> OTHER INFORMATION: motif 2 (figure 2)
<220> FEATURE:
<221> NAME/KEY: MISC_FEATURE
<222> LOCATION: (1)..(1)
<223> OTHER INFORMATION: position 1 is Y, F, R, W or Q
<220> FEATURE:
<221> NAME/KEY: MISC_FEATURE
<222> LOCATION: (4)..(4)
<223> OTHER INFORMATION: position 4 is Y, F, L, I or M
<220> FEATURE:
<221> NAME/KEY: MISC_FEATURE
<222> LOCATION: (5)..(5)
<223> OTHER INFORMATION: position 5 is L, I, M, Q, G, W, S, A or V

<400> SEQUENCE: 99

Xaa Asn Ala Xaa Xaa
 1               5

<210> SEQ ID NO 100
<211> LENGTH: 5
<212> TYPE: PRT
<213> ORGANISM: artificial sequence
<220> FEATURE:
<223> OTHER INFORMATION: motif 3, consensus sequence 3
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (1)..(1)
<223> OTHER INFORMATION: any amino acid, preferably H, E, Q, T, A or I
<220> FEATURE:
<221> NAME/KEY: MISC_FEATURE
<222> LOCATION: (2)..(3)
<223> OTHER INFORMATION: amino acid deletion
<220> FEATURE:
<221> NAME/KEY: MISC_FEATURE
<222> LOCATION: (4)..(4)
<223> OTHER INFORMATION: position 4 is W or V
<220> FEATURE:
<221> NAME/KEY: MISC_FEATURE
<222> LOCATION: (5)..(5)
<223> OTHER INFORMATION: any amino acid, preferably Y, L, M or R

<400> SEQUENCE: 100

Xaa Xaa Xaa Xaa Xaa
 1               5
```